United States Patent [19]

Marburg et al.

[11] Patent Number: 4,695,624

[45] Date of Patent: Sep. 22, 1987

[54] COVALENTLY-MODIFIED POLYANIONIC BACTERIAL POLYSACCHARIDES, STABLE COVALENT CONJUGATES OF SUCH POLYSACCHARIDES AND IMMUNOGENIC PROTEINS WITH BIGENERIC SPACERS, AND METHODS OF PREPARING SUCH POLYSACCHARIDES AND CONJUGATES AND OF CONFIRMING COVALENCY

[75] Inventors: Stephen Marburg, Metuchen; Richard L. Tolman, Warren, both of N.J.; Peter J. Kniskern, Lansdale, Pa.

[73] Assignee: Merck & Co., Inc., Rahway, N.J.

[21] Appl. No.: 719,678

[22] Filed: Apr. 4, 1985

Related U.S. Application Data

[63] Continuation-in-part of Ser. No. 608,738, May 10, 1984, abandoned.

[51] Int. Cl.[4] ............... C07K 15/04; A61K 37/02; A61K 39/02
[52] U.S. Cl. ............... 530/395; 530/402; 530/403; 530/404; 530/405; 530/406; 424/88; 424/92; 536/55.1; 536/1.1; 536/123; 536/54; 435/7; 435/188
[58] Field of Search ............ 424/88, 92; 530/395, 530/402–406; 536/55.1, 1.1, 123, 54

[56] References Cited

U.S. PATENT DOCUMENTS 3,759,890  9/1973  Wilson et al. ............... 424/85
3,969,287  7/1976  Jawerek et al. ............... 530/816
4,175,073  11/1979 Carlsson et al. ............... 435/180
4,185,090  1/1980  McIntire ............... 424/92
4,275,000  6/1981  Ross ............... 424/92
4,356,170  10/1982 Jennings et al. ............... 530/395
4,451,446  5/1984  Vandevelde et al. ............... 536/11
4,459,286  7/1984  Hillemon et al. ............... 424/92

OTHER PUBLICATIONS

Chu et al., *Inf. and Immunity*, 40 (1), 1983, pp. 245–256.
S. Marburg et al., *J Am Chem Society*, 108, 1986, 5282.
Marburg et al., "Limitation of Cyonogen Bromide Activation of Polysaccharides", Merck Sharp and Dohme Res. Lab. publication.

*Primary Examiner*—John Kight
*Assistant Examiner*—Garnette D. Draper
*Attorney, Agent, or Firm*—Richard A. Elder; Hesna J. Pfeiffer; Julian S. Levitt

[57] ABSTRACT

Covalently modified bacterial polysaccharides and proteins; covalent conjugates of such polysaccharides linked by a bigeneric spacer, which permits proof of covalency and facilitates purification of conjugated materials, with immunogenic bacterial membrane or other proteins, which conjugates are useful components of bacterial vaccines; and methods of preparing such polysaccharides, proteins and conjugates and of confirming the covalency of the linkage between polysaccharides and proteins.

20 Claims, No Drawings

COVALENTLY-MODIFIED POLYANIONIC BACTERIAL POLYSACCHARIDES, STABLE COVALENT CONJUGATES OF SUCH POLYSACCHARIDES AND IMMUNOGENIC PROTEINS WITH BIGENERIC SPACERS, AND METHODS OF PREPARING SUCH POLYSACCHARIDES AND CONJUGATES AND OF CONFIRMING COVALENCY

The present application is a continuation-in-part of U.S. patent application, Ser. No. 608,738, filed May 10, 1984, now abandoned.

The present invention is directed to covalently-modified bacterial polysaccharides and immunogenic proteins and to covalent conjugates of such polysaccharides linked by a bigeneric spacer, which permits proof of covalency and facilitates purification and concentration of biologically-desirable entities, with immunogenic bacterial membrane or other proteins, which conjugates are useful components of bacterial vaccines. The present invention also relates to methods of preparing such polysaccharides, proteins and conjugates and methods of confirming the covalency of the conjugate linkage between polysaccharides and proteins.

BACKGROUND OF THE INVENTION

Purified capsular polysaccharides of bacteria have been used to prepare vaccines against the cognate bacteria, but the resulting immune responses have often been less satisfactory than desirable, especially in very young children or individuals with immature or deficient immunological systems. The *Haemophilus influenzae* type b capsular polysaccharide, for example, fails to provoke an immune response in infants, thus making this polysaccharide ineffective by itself in providing protection against the serious pediatric medical problems caused by *H. influenzae* type b bacteria. Enhancement of the immunogenicity of these polysaccharides may often be accomplished by combining them with proteins See, for example, Schneerson et al., "*Haemophilus Influenzae* Type b Polysaccharide-Protein Conjugates:Model for a New Generation of Capsular Polysaccharide Vaccines," New Dev. with Hum. & Vet. Vaccines, 77–94 (1980); Schneerson, et al., J. Exptl. Med., 152, 361 (1980); and Anderson, Infection and Immunity, 39, 233 (1983).

Care must be exercised in the selection of the protein which is to be combined with these polysaccharides, however Certain proteins (e.g., pertussinogen) are non-specific stimulators of the immune system in infants. These proteins can, to a degree, enhance the immune response to polysaccharide antigens, but unfortunately, such non-specific activation leads to unwanted biological effects (i.e., reactogenicity). The much preferred specific enhanced immune responses to these polysaccharide antigens can be achieved in infants by "conjugating" these polysaccharides to appropriate proteins, as first reported by W. F. Goebel and O. T. Avery in 1929 (*J. Exptl. Medicine* 50, 521–531 (1929)).

The means of combining the polysaccharide and protein must also be carefully considered. If, as is believed, the immunological enhancement is realized as a result of the molecular proximity of the polysaccharide determinants to the protein "carrier" determinants, these moieties should not easily separate in the biological system. Non-covalent complexes, arising from the polyanionic character of the polysaccharides and the polycationic character of "carrier" proteins, may stimulate immune responses, but these complexes are chemically labile and the resultant immune responses appear to show T-cell independency. By contrast, covalent conjugates of polysaccharides and protein would possess much greater chemical stability and could demonstrate T-cell dependent immune responses.

Covalent polysaccharide-protein conjugates have been claimed in the literature, but the exact nature of the covalent linkage has not been proven or quantified since the only assay for covalency has been activity in vivo and the processes disclosed in the literature have been difficult to reproduce. *Haemophilus influenzae* type b and *Streptococcus pneumoniae* type 6A polysaccharides were reacted with cyanogen bromide, then with adipic acid dihydrazide, then "coupled" with tetanus toxoid or horseshoe crab hemocyanin proteins in Schneerson et al. J. Exptl. Med., 152, 361 (1980) and Infection and Immunity, 40, 245 (1983). Pneumococcal type 19F polysaccharide was coupled to bovine serum albumin directly by forming imines (Schiff bases) from the reducing ends of the polysaccharides and the pendant amine groups (i.e., lysines) of the protein, then reducing these imines with sodium cyanoborohydride (Lin et al., Immunology, 46, 333 (1982)).

Additionally, polysaccharides linked to diazotized aromatic amines were coupled to the protein's tyrosines in K. K. Nixdorff et al., Immunology 29, 87 (1975) and polysaccharides linked to aromatic amines were converted to isothiocyanates, which were then linked to the pendant amino groups of the protein's lysine in S. B. Svenson and A. A. Lindberg, J. Immunolog. Methods 25, 323 (1979). In each case, however, the resulting conjugate was characterized only by its gel permeation chromatographic behavior. In still another example (S. Nutani et al., Infection and Immunity 36, 971 (1982)), the polysaccharide, pullulan, was activated with cyanuric chloride, then reacted with tetanus toxoid. In this case, the conjugates were characterized by electrophoresis and only shown to be different from the starting materials.

In none of these cases was covalency demonstrated other than by the implications of an aggregated molecular weight, thereby confusing covalency with the interaction of polyanions and polycations in molecular complexes, as these complexes will also give an aggregate molecular weight.

It was therefore an object of this invention to link polysaccharide determinants to protein "carrier" determinants such that the molecular proximity of these moieties could be maintained in biological systems. It was another object of this invention to covalently link capsular polysaccharides with carrier proteins and to develop a method by which the covalent nature of this linkage could be proven and quantified. It was an additional object of this invention to obtain chemically-stable polysaccharide-protein conjugates which demonstrate T-cell dependency and which would be useful as vaccine components for eliciting protective serum antibody to certain bacteria, particularly the cognate bacteria of the polysaccharides used. It was a further object of this invention to develop a method for solubilizing polysaccharides, particularly polyanionic polysaccharides, and covalently-modifying these polysaccharides in preparation for preparing the polysaccharide-protein conjugates. It was one more object of this invention to develop a method of purifying and concentrating covalently-linked polysaccharide-protein conjugates to remove unconjugated macromolecules and excess reactants. It was still a further object of this invention to develop methods of treatment employing these conjugates in immunologically-effective vaccines for use against, e.g., meningitis and otitis media.

SUMMARY OF THE INVENTION

The present invention is directed to covalently-modified bacterial polysaccharides and to chemically-stable conjugates of such polysaccharides with covalently-modified immunogenic membrane proteins, viral protein subunits, synthetic polypeptides, bacterial toxoids or other suitable immunogenic proteins, which conjugates are useful components of immunogenic bacterial vaccines. The polysaccharide-protein conjugates of this invention are coupled through bigeneric spacers containing a covalent thioether group, wherein the bigeneric spacers are atom chains linking macromolecules (such as polysaccharides and proteins), part of which spacers originate with one modified macromolecule (e.g., the covalently-modified polysaccharide) and the other part of which originate with the other modified macromolecule (e.g., the functionalized protein).

In the process according to the instant invention, the polysaccharide is covalently functionalized in one or more steps to produce a polysaccharide with pendant electrophilic centers or pendant thiol groups. Preferably, the polysaccharide is first solubilized in a non-hydroxylic organic solvent, then derivatized with a bifunctional activation agent before being reacted with a bis-nucleophile. The nucleophile-functionalized polysaccharide is then either reacted with a reagent to generate pendant electrophilic sites or reacted with a reagent to generate pendant thiol groups. By proper selection of the bis-nucleophile, i.e., one which would react with the activated polysaccharide and result in a covalently-modified polysaccharide with pendant electrophilic sites or thiol groups, or selection of the proper nucleophile, further functionalization of the nucleophile-functionalized polysaccharide may be avoided.

Independent of the covalent modification of the polysaccharide, the appropriate bacterial "carrier" protein is reacted with reagents generating pendant thiol groups or with reagents generating pendant electrophilic centers, in either a one- or two-step process. The appropriately covalently-modified polysaccharides and proteins are then reacted to form the covalent polysaccharide-protein conjugates and purified to remove unconjugated macromolecules and excess reagents and to permit the immunogenic dosage to be determined based on covalently-linked polysaccharide.

The covalent nature of the linkage may be absolutely proven and defined by cleaving (as by hydrolysis) the polysaccharide from its pendant electrophilic or thiol group moiety, and cleaving the protein from its pendant thiol or electrophilic group moiety, then analyzing for the thioether-containing bigeneric spacer molecule, such that determination of the spacer concentration relative to a marker amino acid (lysine) analysis for the protein determines covalency.

Immunogenic vaccines containing immunologically-effective amounts of the polysaccharide-protein conjugates or their derivatives may then be prepared.

DETAILED DESCRIPTION OF THE INVENTION

The conjugates of the instant invention may be any stable polysaccharide-protein conjugates, coupled through bigeneric spacers containing a thioether group and primary amine, which form hydrolytically-labile covalent bonds with the polysaccharide and the protein. Preferred conjugates according to this invention, however, are those which may be represented by the formulae, Ps-A-E-S-B-Pro or Ps-A'-S-E'-B'-Pro, wherein Ps represents a polysaccharide; Pro represents a bacterial protein; and A-E-S-B and A'-S-E'-B' constitute bigeneric spacers which contain hydrolytically-stable covalent thioether bonds, and which form covalent bonds (such as hydrolytically-labile ester or amide bonds) with the macromolecules, Pro and Ps. In the spacer, A-E-S-B, S is sulfur; E is the transformation product of a thiophilic group which has been reacted with a thiol group, and is represented by

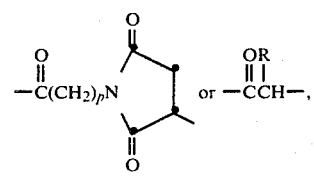

wherein R is H or CH$_3$, and p is 1 to 3; A is

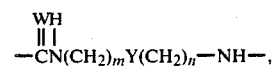

wherein W is O or NH, m is 0 to 4, n is 0 to 3, and Y is CH$_2$, O,S,NR', or CHCO$_2$H, where R' is H or C$_1$- or C$_2$-alkyl, such that if Y is CH$_2$, then both m and n cannot equal zero, and if Y is O or S, then m is greater than 1 and n is greater than 1; and B

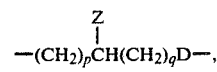

wherein q is 0 to 2, Z is NH$_2$,

COOH, or H, where R' and p are as defined above, and D is

NR',
or

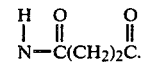

Then in the spacer, A'-S-E'-B', S is sulfur; A' is

wherein a is 1 to 4, and R" is CH$_2$, or

where Y' is NH₂ or NHCOR', and W, p and R' are as defined above, and E' is the transformation product of a thiophilic group which has been reacted with a thiol group, and is represented by

wherein R is as defined above, and B' is

or E' is

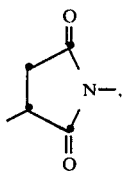

and B' is

wherein p is 1 to 3. Further, of the bigeneric spacers, A-E-S-B and A'-S-E'-B', the E-S-B and A'-S-E' components are determinable and quantifiable, with this identification reflecting the covalency of the conjugate bond linking the side of the thioethersulfur which originates from the covalently modified polysaccharide with the side of the spacer which originates from the functionalized protein.

The polysaccharides of this invention may be any bacterial polysaccharides with acid groups, but are not intended to be limited to any particular types. Examples of such bacterial polysaccharides include *Streptococcus pneumoniae* (pneumococcal) types 6A, 6B, 10A, 11A, 18C, 19A, 19F, 20, 22F, and 23F, polysaccharides; Group B Streptococcus types Ia, Ib, II and III; *Haemophilus influenzae* (H. flu) type b polysaccharide; *Neisseria meningitidis* (meningococcal) groups A, B, C, X, Y, W135 and 29E polysaccharides; and *Escherichia coli* K1, K12, K13, K92 and K100 polysaccharides. Particularly preferred polysaccharides, however, are those capsular polysaccharides selected from the group consisting of H. flu type b polysaccharide, such as described in Rosenberg et al, *J. Biol. Chem.*, 236, 2845–2849 (1961) and Zamenhof et al., *J. Biol. Chem.*, 203, 695–704 (1953); Streptococcus pneumoniae (pneumococcal) type 6B or type 6A polysaccharide, such as described in Robbins et al., *Infection and Immunity*, 26, No. 3, 1116–1122 (Dec., 1979); pneumococcal type 19F polysaccharide, such as described in C. J. Lee et al., *Reviews of Infectious Diseases*, 3, No. 2, 323–331 (1981); and pneumococcal type 23F polysaccharide, such as described in O. Larm et al., *Adv. Carbohyd Chem. and Biochem.*, 33, 295–321, R. S. Tipson et al., ed., Academic Press, 1976.

The proteins according to this invention are those of proven safety and demonstrable immunogenicity, but are not limited to any particular type. Suitable proteins include bacterial membrane proteins; any of various plant proteins, such as edestin or soybean trypsin inhibitor; viral protein subunits, such as hepatitis A or B, herpes gD or gC, Epstein-Barr or varicella zoster subunts; synthetic polypeptides; diphtheria toxoid; or tetanus toxoid, but are preferably *Neisseria meningitidis* (meningococcal) B serotype outer membrane proteins, which are T-cell stimulators. An example of these serotype proteins has been described in Helting et al., "Serotype Determinant Proteins of *Neisseria Meningitidis*", Actapath. Microbiol. Scand. Sect. C, 89, 69–78 (1981), and Frasch et al., J. Bact., 127, 973–981 (1976).

Then the conjugates, Ps-A-E-S-B-Pro, according to this invention may contain spacers whose components include derivatives of, inter alia: carbon dioxide, 1,4-butanediamine, and S-carboxymethyl-N-acetylhomocysteine; carbon dioxide, 1,5-pentanediamine, and S-carboxymethyl-N-acetylhomocysteine; carbon dioxide, 3-oxa-1,5-pentanediamine, and S-carboxymethyl-N-acetylhomocysteine; carbon dioxide, 1,4-butanediamine, and S-carboxymethyl-N-acetylcysteine; carbon dioxide, 1,3-propanediamine, and S-carboxymethyl-N-benzoylhomocysteine; carbon dioxide, 3-aza-1,5-pentanediamine, and S-carboxymethyl-N-acetylcysteine; and carbon dioxide, 1,2-ethanediamine, glycine, and S-(succin-2-yl)-N-acetylhomocysteine. The conjugates, Ps-A'-S-E'-B'-Pro, according to this invention, may contain spacers whose components include derivatives of, inter alia: carbon dioxide and S-carboxymethylcysteamine; carbon dioxide and S-(α-carboxyethyl)cysteamine; carbon dioxide and S-carboxymethylhomocysteamine; carbon dioxide, S-(succin-2-yl)cysteamine, and glycine; and carbon dioxide and S-carboxymethylcysteine.

In the process of the instant invention, the polysaccharide is covalently-modified by (a) solubilizing it in a non-hydroxylic organic solvent, then (b) activating it with a bifunctional reagent, (c) reacting this activated polysaccharide with a bis-nucleophile, and finally, if necessary, further (d) functionalizing this modified polysaccharide by either reaction, (i) with a reagent generating electrophilic (e.g., thiolphilic) sites or, (ii) with a reagent generating thiol groups. The protein is conversely either reacted (i) with a reagent generating thiol groups or (ii) with a reagent generating thiolphilic sites, then the covalently-modified polysaccharide and the functionalized protein are reacted together to form the stable covalently-bonded conjugate and the final mixture is purified to remove unreacted polysaccharides and proteins.

The process of this invention also includes selection of a nucleophile or bis-nucleophile which will react with the activated polysaccharide to form a covalently-modified polysaccharide with pendant electrophilic sites or pendant thiol groups, thereby obviating the need to further functionalize the bis-nucleophile-modified polysaccharide prior to reacting the covalently-modified polysaccharide with the covalently-modified protein. Also, the functionalization of the protein to either moiety form may be accomplished in more than one step according to the selection of reactants in these steps.

A. PREPARATION OF THE POLYSACCHARIDE

In the first step toward covalently-modifying the polysaccharide, the solid polysaccharide must be solubilized.

Since the nucleophilic alcoholic hydroxyl groups of a polysaccharide cannot compete chemically for electrophilic reagents with the hydroxyls of water in an aqueous solution, the polysaccharide should be dissolved in non-aqueous (non-hydroxylic) solvents. Suitable solvents include dimethylformamide, dimethylsulfoxide, dimethylacetamide, formamide, N,N'-dimethylimidazolidinone, and other similar polar, aprotic solvents, preferably dimethylformamide.

In addition to the use of these solvents, Applicants have found that converting the polysaccharides of their invention (e.g., the capsular polysaccharides of *H. influenzae* type b, which are a ribose-ribitol phosphate polymers, and of pneumococcal types 6B, 19F and 23F), which have acid hydrogens, such as phosphoric acid mono- and diesters, into an appropriate salt form, these polysaccharides become readily soluble in the above solvents. The acidic hydrogens in these macromolecules may be replaced by large hydrophobic cations, such as tri- or tetra-($C_1$-to $C_5$) alkylammonium, 1-azabicyclo[2.2.2]octane,1,8-diazabicyclo [5.4.0]undec-7-ene or similar cations, particularly tri- or tetra-($C_1$-to $C_5$) alkylammonium, and the resultant tri- or tetraalkylammonium or similar salts of phosphorylated polysaccharides readily dissolve in the above solvents at about 17°–50° C., while being stirred for from one minute to one hour.

Partially-hydrolyzed *H. influenzae* type b polysaccharide has been converted into the tetrabutylammonium salt, then dissolved in dimethylsulfoxide (Egan et al., *J. Amer. Chem. Soc.*, 104, 2898 (1982)), but this product is no longer antigenic, and therefore useless for preparing vaccines. By contrast, Applicants accomplish the solubilization of an intact, unhydrolyzed polysaccharide by passing the polysaccharide through a strong acid cation exchange resin, in the tetraalkylammonium form, or by careful neutralization of the polysaccharide with tetraalkylammonium hydroxide, preferably by the former procedure, and thereby preserve the viability of the polysaccharide for immunogenic vaccine use.

Subsequent steps are then directed to overcoming the other significant physico-chemical limitation to making covalent bonds to polysaccharides, that being the lack of functional groups on the polysaccharides, other than hydroxyl groups, which are reactive enough with reagents commonly or practically used for functionalization of units with which bonding is desired. Activation of the polysaccharide to form an activated polysaccharide, reaction with bis-nucleophiles to form a nucleophile-functionalized polysaccharide, and functionalization with reagents generating either electrophilic sites or thiol groups, are all directed to covalently-modifying the polysaccharide and developing functional groups on the polysaccharide in preparation for conjugation.

In the next step, the solubilized polysaccharide is activated by reaction with a bifunctional reagent at about 0°–50° C., while stirring for ten minutes to one hour, with the crucial weight ratio of activating agent to polysaccharide in the range of 1:5 to 1:12. In the past, this activation has been accomplished by reaction of the polysaccharide with cyanogen bromide. However, derivatives activated with cyanogen bromide, which has a "proclivity" for vicinal diols, have shown transient stability during dialysis against a phosphate buffer. Therefore, while activation with cyanogen bromide is still possible according to the present invention, this reagent is poorly utilized in activation of polysaccharides and is not preferred. Instead, preferred bifunctional reagents for activating the polysaccharide include carbonic acid derivatives

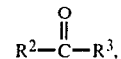

whrein $R^2$ and $R^3$ may be independently, azolyl, such as imidazolyl; halides; or phenyl esters, such as p-nitrophenyl, or polyhalophenyl.

Carbonyldiimidazole, a particularly preferred reagent, will react with the hydroxyl groups to form imidazolylurethanes of the polysaccharide, and arylchloroformates, including, for example, nitrophenylchloroformate, will produce mixed carbonates of the polysaccharide. In each case, the resulting activated polysaccharide is very susceptible to nucleophilic reagents, such as amines, and is thereby transformed into the respective urethanes.

In the next stage, the activated polysaccharide is reacted with a nucleophilic reagent, such as an amine, particularly diamines, for example,

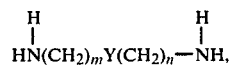

wherein m is 0 to 4, n is 0 to 3, and Y is $CH_2$, O, S, NR', $CHCO_2H$, where R' is H or a $C_1$- or $C_2$-alkyl, such that if Y is $CH_2$, then both m and n cannot equal zero, and if Y is O or S, then m is greater than 1, and n is greater than 1, in a gross excess of amine (i.e., for example, a 50- to 100-fold molar excess of amine vs. activating agent used). The reaction is kept in an ice bath for from 15 minutes to one hour then kept for 15 minutes to one hour at about 17° to 40° C.

An activated polysaccharide, when reacted with a diamine, e.g., 1,4-butanediamine, would result in a urethane-form polysaccharide with pendant amines, which may then be further functionalized by acylating. Mixed carbonates will also readily react with diamines to result in pendant amine groups.

Alternatively, the activated polysaccharide may be reacted with a nucleophile, such as a monohaloacetamide of a diaminoalkane, for example, 4-bromoacetamidobutylamine (see, W. B. Lawson et al., *Hoppe Seyler's Z. Physiol Chem.*, 349, 251 (1968)), to generate a covalently-modified polysaccharide with pendant electrophilic sites. Or, the activated polysaccharide may be reacted with an aminothiol, such as cysteamine (aminoethanethiol) or cysteine, examples of derivatives of which are well-known in the art of peptide synthesis, to produce a polysaccharide with pendant thiol groups. In both cases, no additional functionalization is necessary prior to coupling the covalently-modified polysaccharide to the modified bacterial "carrier" protein.

The last step in preparing the polysaccharide, the further functionalization, if necessary, of the polysaccharide, may take the form of either reacting the nucleophile-functionalized polysaccharide with a reagent to generate electrophilic (i.e., thiophilic) sites, or with a reagent to generate thiol groups.

Reagents suitable for use in generating electophilic sites, include for example, those for acylating to α-haloacetyl or α-halopropionyl, derivative such as

wherein R is H or CH$_3$; X is Cl, Br or I; and X' is nitrophenoxy, dinitrophenoxy, pentachlorophenoxy, pentafluorophenoxy, halide, O-(N-hydroxysuccinimidyl) or azido), particularly chloroacetic acid or α-bromopropionic acid, with the reaction being run at a pH of 8 to 11 (maintained in this range by the addition of base, if necessary) and at a temperature of about 0° to 35° C., for ten minutes to one hour. An amino-derivatized polysaccharide may be acylated with activated maleimido amino acids (see, O. Keller et al, Helv. Chim. Acta., 58, 531 (1975)) to produce maleimido groups,

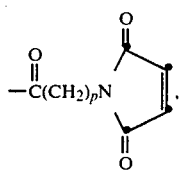

wherein p is 1 to 3; with a 2-haloacetyling agent, such as p-nitrophenylbromoacetate; or with an α-haloketone carboxylic acid derivative, e.g.,

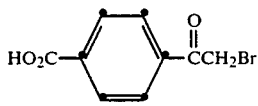

(Ber., 67, 1204, (1934)) in order to produce appropriately functionalized polysaccharides susceptible to thio substitution.

Reagents suitable for use in generating thiol groups include, for example, acylating reagents, such as thiolactones, e.g.,

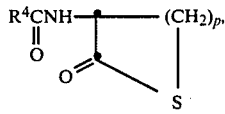

wherein R$^4$ is C$_1$- to C$_4$-alkyl or mono- or bicyclic aryl, such as C$_6$H$_5$ or C$_{10}$H$_{13}$, and p is 1 to 3;

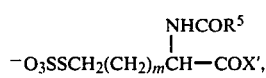

wherein m is 0 to 4, R$^5$ is C$_1$- to C$_4$-alkyl or C$_6$H$_5$, and X' is as defined above, followed by treatment with HSCH$_2$CH$_2$OH; or

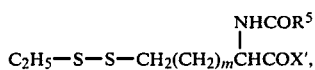

wherein m, R$^5$ and X' are as defined immediately above, then treatment with dithiothreitol. Such reactions are carried out in a nitrogen atmosphere, at about 0° to 35° C. and at a pH of 8 to 11 (with base added, as necessary, to keep th pH within this range), for one to twenty-four hours. For example, an amino-derivatized polysaccharide may be reacted with

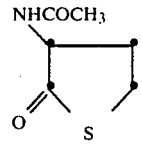

to produce an appropriately-functionalized polysaccharide.

By these steps then, covalently-modified polysaccharides of the forms, Ps-A-E*- or Ps-A'-SH-, wherein E* is —CCHX or

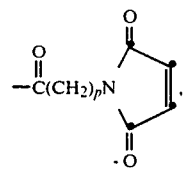

and A, A', R, X and p are as defined above, are produced.

B. PREPARATION OF THE PROTEIN

Separate functionalization of the protein to be coupled to the polysaccharide, involves reaction of the protein with one or more reagents to generate a thiol group, or reaction of the protein with one or more reagents to generate an electrophilic (i.e., thiophilic) center.

In preparation for conjugation with an electrophilic-functionalized polysaccharide, the protein is reacted in one or two steps with one or more reagents to generate thiol groups, such as those acylating reagents used for generating thiol groups on polysaccharides, as discussed on pages 15–17 above. Thiolated proteins may also be prepared by aminating carboxy-activated proteins, such as those shown in Atassi et al., Biochem et Biophys. Acta, 670, 300, (1981), with aminothiols, to create the thiolated protein. A preferred embodiment of this process step involves the direct acylation of the pendant amino groups (i.e., lysyl groups) of the protein with N-acetylhomocysteinethiolactone at about 0° to 35° C. and pH 8-11, for from five minutes to two hours, using equiweights of reactants.

When E'B' is

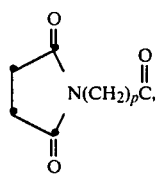

the conditions and method of preparing the functionalized protein are as discussed above on pages 15–17 for preparing the counterpart polysaccharide by reaction with activated maleimido acids.

In preparing for conjugation with a covalently-modified bacterial polysaccharide with pendant thiol groups, the protein is acylated with a reagent generating an electrophilic center, such acylating agents including, for example,

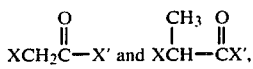

wherein X and X' are as defined above; and

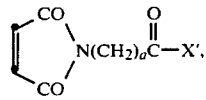

wherein X' is as defined above. Suitable proteins with electophilic centers also include, for example, those prepared by acylation of the pendant lysyl amino groups with a reagent, such as activated maleimido acids, for example,

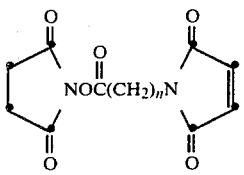

or by reacting the carboxy-activated protein with monohaloacetyl derivatives of diamines. In both preparation reactions, the temperature is from 0° to 35° C. for from five minutes to one hour and the pH is from 8 to 11.

C. FORMATION OF THE CONJUGATE

Formation of the conjugate is then merely a matter of reacting any of the covalently-modified polysaccharides having pendant electrophlic centers with any of the proteins having pendant thiol groups at a pH of 7 to 9, in approximate equiweight ratios, in a nitrogen atmosphere, for from six to twenty-four hours at from about 17° to 40° C., to give a covalent conjugate. Examples of such reactions include:

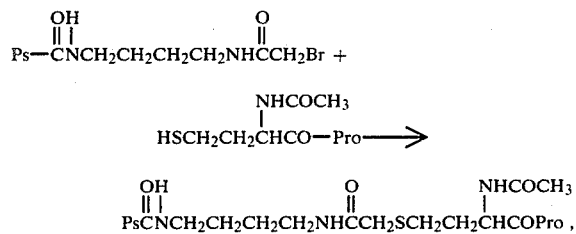

wherein an activated polysaccharide which has been reacted with 4-bromoacetamidobutylamine as reacted with a protein which has been reacted with N-acetylhomocysteinethiolactone, to form a conjucate, and:

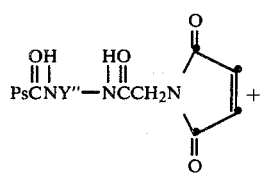

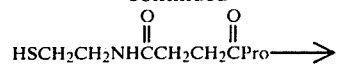

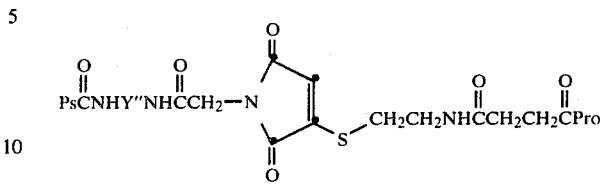

(where Y''' is a $C_2$–$C_8$alkyl radical), wherein an amino-derivatized polysaccharide which has been reacted with acitvated maleimido acids is reacted with a carboxy-activated protein which has been aminated with an aminothiol, to form a conjugate.

Similarly, any of the covalently-modified polysaccharides with pendent thiol groups may be reacted with any of the proteins having pendant electrophilic centers to give a covalent conjugate. An example of such a reaction is:

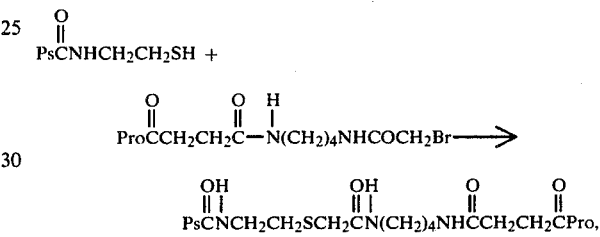

wherein an activated polysaccharide which has been reacted with an aminothiol is reacted with a carboxy-activated protein which has been reacted with monohaloacetyl derivatives of a diamine, to form a conjugate.

Should the electrophilic activity of an excess of haloacetyl groups need to be eliminated, reaction of the conjugate with a low molecular weight thiol, such as n-acetylcysteamine, will accomplish this purpose. Use of this reagent, n-acetylcysteamine, also allows confirmation accounting of the haloacetyl moieties used (see Section D), because the S-carboxymethylcysteamine which is formed may be uniquely detected by the method of Spackman, Moore and Stein.

These conjugates are then centrifuged at about 100,000 X G using a fixed angle rotor for about two hours at about 1° to 20° C., or are submitted to any of a variety of other purification procedures, including gel permeation, ion exclusion chromatography, gradient centrifugation, or other differential adsorption chromatography, to remove non-covalently-bonded polysaccharides and proteins, using the covalency assay for the bigeneric spacer (see below) as a method of following the desired biological activity.

The further separation of reagents may be accomplished by size-exclusion chromatography in a ( column, or in the case of very large, non-soluble proteins, such as *N. meningitidis* B serotype outer membrane protein, this separation may be accomplished by ultracentrifugation.

D. ANALYSIS TO CONFIRM COVALENCY

Analysis of the conjugate to confirm the covalency, and hence the stability of the conjugate, is accomplished by Applicants by hydrolyzing (preferably with 6N HCl at 110° C. for 20 hours) the conjugate, then quantitatively analyzing for the amino acid of the hydrolytically-stable spacer containing the thioether bond and constituent amino acids of the protein. The contribution of the amino acids of the protein may be removed, if necessary, by comparison with the appropriate amino acid standard for the protein involved, with the remaining amino acid value reflecting the covalency of the conjugate, or the amino acid of the spacer may be designed to appear outside the amino acid standard of the protein in the analysis. The covalency assay is also useful to monitor purification procedures to mark the enhancement of concentration of the biologically-active components. In the above examples, hydrolysis of

results in the release of S-carboxymethylhomocysteine,

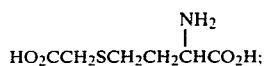

hydrolysis of

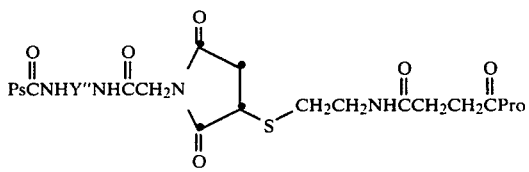

results in the release of the aminodicarboxylic acid,

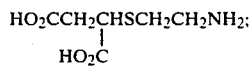

and hydrolysis of

results in the release of S-carboxymethylcysteamine, $H_2NCH_2CH_2SCH_2CO_2H$ by cleavage of the Ps-A-E-S-B-Pro molecule at peptide linkages and other hydrolytically-unstable bonds. Chromatographic methods, such as those of Spackman, Moore, and Stein, may then be conveniently applied and the ratio of amino acid constituents determined.

E. APPLICATIONS

One or more of the conjugates of this invention may be used in mammalian species for either active or passive protection prophylactically or therapeutically against bacteremia caused by the cognate organism, such as, in the preferred embodiments of this invention, *Haemophilus influenzae* type b or *Streptococcus pneumoniae* type 6B, 19F or 23F organisms. Active protection may be accomplished by injecting an effective amount (a quantity capable of producing measurable amounts of antibodies, e.g., 2 to 50 μg) of polysaccharide in the conjugate form of each of the conjugates being administered per dose, whole antiserum obtained from animals previously dosed with the conjugate or conjugates, or globulin or other antibody-containing fractions of said antisera, with or without a pharmaceutically-acceptable carrier, such as aseptic saline solution. Such globulin is obtained from whole antiserum by chromatography, salt or alcohol fractionation or electrophoresis. Passive protection may be accomplished by standard monoclonal antibody procedures or by immunizing suitable mammalian hosts. The use of an adjuvant (e.g., alum) is also intended to be within the scope of this invention.

In a preferred embodiment of this invention, the conjugate is used for active immunogenic vaccination of humans, especially infants and children. For additional stability, these conjugates may also be lyophilized in the presence of lactose (for example, at 20 μg/ml of H. flu polysaccharide/4 mg/ml lactose or 50 μg/ml of pneumococcal polysaccharide/10 mg/ml lactose) prior to use.

A preferred dosage level is an amount of each of the conjugates or derivative thereof to be administered corresponding to 25 μg of polysaccharide in the conjugate form for conjugates of pneumococcal polysaccharides and 10 μg of polysaccharide in the conjugate form for conjugates of H. flu type b polysaccharide in a single administration. If necessary, an additional one or two doses of conjugate or derivative thereof of the *H. influenzae* type b polysaccharide in an amount corresponding to 10 μg of the polysaccharide in the conjugate form, may also be administered.

The invention is further defined by reference to the following examples, which are intended to be illustrative and not limiting.

EXAMPLE 1

PREPARATION OF *H. INFLUENZAE* TYPE b CAPSULAR POLYSACCHARIDE (PRP)

INOCULUM AND SEED DEVELOPMENT

A Stage:

A lyophilized tube of *Haemophilus influenzae* type b, (cultured from Ross 768, received from State University of New York) was suspended in 1 ml of sterile Haemophilus inoculum medium (see below) and this suspension was spread on nineteen Chocolate Agar Plates (BBL). After 20 hours incubation at 37° C. in a candle jar, the growth on each plate was resuspended in 1-2 ml Haemophilus inoculum medium and pooled.

| Haemophilus Inoculum Medium* | |
|---|---|
| Soy Peptone | 10 gm/liter |
| NaCl | 5 gm/liter |
| $NaH_2PO_4$ | 3.1 gm/liter |
| $Na_2HPO_4$ | 13.7 gm/liter |
| $K_2HPO_4$ | 2.5 gm/liter |
| Distilled Water | To Volume |

*The pH of the solution is adjusted to a target value of 7.2 ± 0.1 (a typical value was pH 7.23) and the solution was sterilized by autoclaving at 121° C. for 25 minutes.

B Stage: 2-Liter Non-baffled Erlenmeyer Flasks

One-third portions of the resuspended bacteria from "A stage" (above) were used to inoculate three two-liter flasks, each containing about 1.0 liter of complete Haemophilus seed and production medium (see below). The flasks were then incubated at 37° C. on a rotary shaker of 200 rpm for about 5 hours. A typical $OD_{660}$ value at the end of the incubation period was 0.37.

| Complete Haemophilus Seed & Production Medium | |
| --- | --- |
| $NaH_2PO_4$ | 3.1 g/l |
| $Na_2HPO_4$ | 13.7 g/l |
| Soy Peptone | 10 g/l |
| Yeast extract diafiltrate (1) | 10 ml/l |
| $K_2HPO_4$ | 2.5 g/l |
| NaCl | 5.0 g/l |
| Glucose (2) | 5.0 g/l |
| Nicotinamide adenine dinucleotide (NAD) (3) | 2 mg/l |
| Hemin (4) | 5 mg/l |

The salts and soy peptone were dissolved in small volumes of hot, pyrogen-free water and brought to correct final volume with additional hot, pyrogen-free water. The fermenters or flasks were then sterilized for about 25 minutes at 121° C. and after cooling, yeast extract diafiltrate (1), glucose (2), NAD (3), and hemin (4) were added aseptically to the flasks or fermenters prior to inoculation.
(1) Yeast extract diafiltrate: 100 g brewers' yeast extract (Amber) was dissolved in 1 liter distilled water and ultrafiltered in an Amicon DC-30 hollow fiber with H10X50 cartridges to remove molecules with m.w. 50,000. The filtrate was collectedand passed through a 0.22µ membrane as a sterile product.
(2) Glucose was prepared as a sterile 25% solution in glass-distilled water.
(3) A stock solution of NAD containing 20 mg/ml was sterilized by filtration through a Millipore filter (0.22µ) and added aseptically just prior to inoculation.
(4) A stock solution of Hemin 3X was prepared by dissolving 200 mg in 10 ml of 0.1 M NaOH and the volume adjusted with distilled, sterilized water to 100 ml. The solution was sterilized for 20 minutes at 121° C. and added aseptically to the finalmedium prior to inoculation.

C-STage: 70-Liter Seed Fermenter

Three liters of the product of B Stage was used to inoculate a 70-liter fermenter containing 41.4 liters of Complete haemophilus Seed & Production medium (prepared as descrived above) and 17 ml UCON B625 antifoam. The pH started at 7.4.

The fermentation was maintained at 37° C. with 100 rpm agitation and monitored by optical density (O.D.) and pH determinations until a typical O.D. of 0.39 was reached (after about 5.5 hours).

D Stage: 800-Liter Production Fermenter

Approximately 40 liters of the product of "C Stage" was used to inoculate an 800-liter fermenter containing 570 liters of production medium (prepared as described above), scaled to the necessary volume and 72 of UCON LB625 antifoam.

The fermentation was maintained at 37° C. with 100 rpm of agitation, with the O.D. and pH levels being checked about every two hours until the O.D. was similar for a two-hour period, at which time the fermentation was terminated (a typical final O.D. was 0.54 after 12 hours).

HARVEST AND INACTIVATION

Approximately 600 liters of the batch was inactivated by harvesting into a "kill tank" containing 12 liters of 1% thimerosal.

CLARIFICATION

After 18 hours inactivation at 4° C., the batch was centrifuged in 4-in. bowl Sharples centrifuges at a flow rate adjusted to maintain product clarity (variable between 1.3 and 3.0 liters/min.) The supernatant obtained after centrifugation (15,000 rpm) was used for product recovery.

ISOLATION AND CONCENTRATION BY ULTRAFILTRATION

The supernatant fluid from two production fermentations was pooled and concentrated at 2°-8° C. in a Romicon ultrafiltration unit with ten (50,000 Daltons cut-off) hollow fiber cartridges (4.5 m² membrane area; 2.0 lpm air flow and 20 psi; concentration such that after approximately 4.5 hours, 1200 liters had been concentrated to 32.5 liters. The filtrate was discarded.

48 and 61% ETHANOL PRECIPITATION

To the 32.5 liters of Romicon retentate, 30 liters of 95% ethanol was added dropwise over 1 hour with stirring at 4° C. to a final concentration of 48% ethanol by volume. The mixture was stirred two additional hours at 4° C. to ensure complete precipitation, and the supernatant fluid was collected through a single 4-inch Sharples centrifuge at 15,000 rpm (flow rate =0.27 liters/min). The insoluble pellet was discarded and the clarified fluid was brought to 61% ethanol with the addition of 20.8 liters of additional 95% ethanol over a one hour period. The mixture was stirred for three additional hours to insure complete precipitation.

RECOVERY OF THE SECOND PELLET

The resulting 48% ethanol soluble-61% ethanol-insoluble precipitate was collected by centrifugation in the 4-inch Sharples centrifuge at 15,000 rpm (flow rate =0.62 liters/min.) and the 61% ethanol supernatant fluid was discarded. The crude product yield was 0.377 kg of wet paste.

CALCIUM CHLORIDE EXTRACTION

The 377 grams of 61% ethanol-insoluble material, was mixed in a Daymax dispersion vessel at 2°-8° C. with 6.5 liters of cold, glass-distilled water. To this mixture, 6.5 liters of cold 2M $CaCl_2.H_2O$ was added, and the mixture (final concentration =1.0M $CaCl_2$) was extracted at 4° C. for 15 minutes. The vessel was then rinsed out with 2 liters of 1M $CaCl_2.2H_2O$, resulting in 15 liters final volume.

23% ETHANOL PRECIPITATION

The 15 liters of $CaCl_2$ extract from above was brought to 23% ethanol by adding 4.48 liters of 95% ethanol dropwise, with stirring, at 4° C. over 30 minutes. After additional stirring for 17 hours, the mixture was centrifuged through a K2 Ultracentrifuge at 25,000 rpm (flow rate =165 ml/min) for 6.5 hours at 4° C. The supernatant fluid was decanted through cheese cloth to remove lipid-like floating material and the insoluble pellet was discarded.

37% ETHANOL PRECIPITATION AND COLLECTION OF CRUDE PRODUCT PASTE

The 23% ethanol-soluble supernatant fluid was brought to 37% ethanol by the addition of 4.33 liters of 95% ethanol, dropwise with stirring, over a 30 minute period. The mixture was then allowed to stand with agitation for one hour, then without agitation for 14 hours, to ensure complete precipitation. The resulting mixture was then centrifuged in a 4-inch Sharples unit at 15,000 rpm (flow rate =0.2 liters/minute) to collect the pelleted crude polysaccharide.

TRITURATION

The pellet from the centrifugation was transferred to a 1-gallon Waring-Blender containing 1 liter of absolute alcohol and blended for 30 seconds at the highest speed. Blending was continued at 30 seconds on and 30 seconds off until a hard, white powder resulted. The powder was collected on a Buchner funnel with a teflon filter disc and washed sequentially in situ with two 1-liter portions of absolute ethanol and two 2-liter portions of acetone. The material was then dried in vacuo, at 4° C., for 24 hours, resulting in 68 g (dry weight) of product.

PHENOL EXTRACTION

The 68 grams of dry material from the trituration step was resuspended in 12 liters of 0.488 M sodium acetate, pH 6.9, with the aid of a Daymax dispersion vessel. The sodium acetate solution was immediately extracted with 4.48 liters of a fresh aqueous phenol solution made as follows: 900 ml of 0.488 M sodium acetate, pH 6.9, was added to a five-pound bottle of phenol (Mallinckrodt crystalline) in a 20-liter pressure vessel and mixed until a complete solution was effected. Each phenol extract was centrifuged for 2½ hours at 30,000 rpm and 4° C. in the K2 Ultracentrifuge (Electronucleonics) in order to break the emulsion. The aqueous effluent was extracted three additional times with 3.2 fresh aqueous phenol solution in a similar manner. The phenol phases were discarded.

DIAFILTRATION

The aqueous phase from the phenol extractions above (17.6 liters) was diluted with 300 liters of cold, glass-distilled water and diafiltered at 4° C. on an Amicon DC-30 ultrafiltration apparatus using 3 H10P10 cartridges. The Amicon unit was rinsed and and the rinse added to the retentate, such that the final volume was 17.5 liters. The ultrafiltrate was discarded.

67% ETHANOL PRECIPITATION 0.438 liters of 2.0 M $CaCl_2$ was added to the 17.5 liters of dialysate from the previous step (final $CaCl_2$ concentration was 0.05 M) and the solution was made 67% ethanol with dropwise addition over one hour of 35.88 liters of 95% ethanol to the rapidly-stirring solution. After 4 hours of agitation, then standing for 12 hours more at 4° C., the clear supernatant fluid was siphoned off and the precipitate was collected by centrifugation in the 4-inch Sharples centrifuge (15,000 rpm), at 4° C. for 45 min. The resulting polysaccharide pellet was triturated in a 1-gallon Waring blender using the 30 seconds on-30 seconds off method with 2 liters of absolute ethanol, collected on a Buchner funnel fitted with a teflon filter disc, and washed in situ with four 1-liter portions of absolute ethanol followed by two 1-liter portions of acetone. The sample was then dried in a tared dish in vacuo at 4° C. for 20 hours. The yield was 39 grams of dry powder.

ULTRACENTRIFUGATION IN 20% ETHANOL AND COLLECTION OF FINAL PRODUCT

The 39 grams of dry powder from above was dissolved in 15.21 liters of distilled water, to which was added 0.39 liters of 0.05M $CaCl_2 0.2H_2O$, bringing the solution to 0.05M $CaCl_2$ and the total volume to 15.6 liters (2.5 mg polysaccharide/ml), and the mixture was brought to 24% ethanol with the dropwise addition of 4.93 liters of 95% ethanol over 30 minutes. The mixture was clarified immediately by centrifugation in a K2 Ultracentrifuge containing a K3 titanium bowl and a K11 Noryl core (30,000 rpm and 100 ml/min) for 3.5 hrs at 4° C. The pellet was discarded and the clear supernatant fluid (volume =19.8 liters) was brought to 37% ethanol by the addition of 4.23 liters of 95% ethanol over 30 minutes with agitation. After stirring 30 additional minutes, the mixture was allowed to stand without agitation at 4° C. for 17 hours and, then collected through a 4-inch Sharples centrifuge at 15,000 rpm (45 minutes was required).

The resulting paste was transferred to a 1-gallon Waring blender containing 2 liters of absolute ethanol and blended at the highest speed 4 or 5 cycles of 30 seconds on-30 seconds off, until a hard, white powder formed. This powder was collected on a Buchner funnel with a Zitex teflon disc and rinsed sequentially in situ with two fresh 0.5-liter portions and one 1-liter portion of absolute ethanol, and with two 1-liter portions of acetone. The product was removed from the funnel and transferred to a tared dish for drying in vacuo at 4° C. (for 25½ hours). The final yield of the product was 34.7 grams dry weight, and its properties were as follows:

TABLE 1-1

HIb POLYSACCHARIDE CHEMICAL ASSAY DATA

| Assay | Result |
|---|---|
| Moisture (TG) | 13.5% |
| Protein | 0.0% |
| Nucleic Acid | 1.3% |
| Ribose (pentose) | 35.1% |
| Phosphorus | 7.8% |
| $K_D$ (Sepharose 4B) | .05 .35 |
| $K_D$ (Sepharose 2B) | .43 .60 |

The following procedures were used in performing the assays.

1. Moisture—Standard thermogravimetry (wt. loss to 100° C.) using a Perkin-Elmer thermobalance TSG-1.
2. Protein—Lowry method; Lowry et al., J. Biol. Chem., 193: 265 (1951).
3. Nucleic Acid—U. V. method; Warburg and Christian, Biochem Z., 310: 384 (1942).
4. Ribose—Bial method; Dische and Schwartz, Mickorochim Acta 2:13 (1937).
5. Phosphorus—Molybdate method; Chen et al., Anal. Chem. 28: 1756 (1956).
6. $K_D$—Determined on Sepharose 4B using refractive index.

TABLE 1-2

PYROGENIC SUBSTANCES TEST (HIb Polysaccharide)

| Concentration (mcg/ml/kg) | Max. Temp. Rise* 0° C. (3 rabbits) |
|---|---|
| 0.1 (polysac.) | 0.2, 0.2, 0.1 |

*1.0 ml/kg dose

The polysaccharide was further identified by Agar Gel Diffusion as follows: Double diffusion on agar (Ouchterlony) was performed using Hyland pattern D plates. Antiserum prepared against the Ross 768 strain of *H. influenzae* was placed in the center wells while the bulk polysaccharide, at concentrations of 50, 25, 12.5, 6.2 and 3.1 mcg/ml, was placed in the satellite wells. The plate was incubated at 20°-25° C. in a moist chamber for 24 hours. Precipitin bands were observed between the bulk polysaccharide and the specific antiserum at polysaccharide concentrations of 50, 25 and 12.5 mcg/ml.

EXAMPLE 2

PREPARATION OF NEISSERIA MENINGITIDIS B11 SEROTYPE 2 MEMBRANE PROTEIN

A. Fermentation

1. *Neisseria meningitidis* Group B11

A tube containing the lyophilized culture of *Neisseria meningitidis* (obtained from Dr. M. Artenstein, Walter Reed Army Institute of Research (WRAIR), Washington, D.C.) was opened and Eugonbroth (BBL) was added. The culture was streaked onto Chocolate agar plates (BBL) and incubated at 37° C. with 5% $CO_2$ for 36 hours, at which time the growth was harvested into 10% skim milk medium (Difco), aliquoted and frozen at −70° C. The organism was positively identified by agglutination with specific antiserum supplied by WRAIR and typing serum supplied by Difco.

This first-passage culture was streaked onto Chocolate agar plates and incubated at 37° C. with 5% $CO_2$ for 18 hours, at which time the growth was harvested into 10% skim milk medium, aliquoted into 1 ml amounts and frozen at −70° C. The organism was again positively identified by agglutination with specific antiserum supplied by WRAIR and typing serum supplied by Difco.

A vial of the culture from the second passage was thawed and streaked onto 10 Columbia Sheep Blood agar plates (CBAB-BBL). The plates were incubated at 37° C. with 5% $CO_2$ for 18 hours, after which time the growth was harvested into 100 ml of 10% skim milk medium, aliquoted in 0.5 ml amounts and frozen at −70° C. The organism was positively identified by agglutination with specific antiserum, sugar fermentation and gram stain.

A vial of the culture from this this passage was thawed, diluted with Mueller-Hinton Broth and streaked onto 40 Mueller-Hinton agar plates. The plates were incubated at 37° C. with 6% $CO_2$ for 18 hours after which time the growth was harvested into 17 ml of 10% skimmed milk medium, aliquoted in 0.3 ml amounts and frozen at −70° C. The organism was positively identified by Gram stain, agglutination with specific antiserum and the oxidase test.

2. Fermentation and collection of cell paste a. Inoculum Development: The inoculum was grown from two 0.5 ml frozen vials of *Neisseria meningitidis* Group B, B-11 from above (passage 4). Four Mueller-Hinton agar Blake bottles were inoculated, harvested approximately 18 hours later, and used as an inoculum for 5 liters of Gotschlich's yeast dialysate medium at pH 7.29. The O.D. was adjusted to 0.065 at 660 nm (Perkin Elmer). The organism was grown in 5 two-liter Erlenmeyer flasks (each containing 1 liter of medium; see below) at 37° C. in a shaker. The O.D. was monitored at 45-, 75- and 120minute intervals. Approximately 4 liters of broth culture, at an $O.D._{0.660}$ of 0.81 (Spectronic 20), resulted.

A 3 ml sample was taken for Gram stain, isolation streakes onto CBAB, Mueller, Hinton, and yeast extract dextrose plates and agglutination check. All reactions were satisfactory.

b. 70 Liter Seed Fermenter: Approximately 3600 ml of seed culture was used to inoculate a sterile 70-liter fermenter containing 42.6 liters of complete production medium (see below).

The conditions for the 70-liter fermentation included 37° C., 185 rpm with 10 liters/minute air sparging and constant pH control at pH 7.0 for 5.5 hours.

The culture was plated onto Mueller-Hinton agar plates, yeast extract dextrose and rabbit blood agar plates (Merck) at 37° C. and tested for agglutination with *N. meningitidis* group B antiserum. The growth on Mueller-Hinton agar plates, yeast extract dextrose plates and rabbit blood agar plates was normal and the agglutination reaction was positive. For this batch, the final O.D. was 0.840 at 660 microns after 5.5 hours.

c. 800-Liter Production Fermenter: Approximately 46.2 liters of seed culture were used to inoculate a sterile 800 liter fermenter containing 568.2 liters of complete production medium (see below). The batch was incubated at 37° C., 100 rpm with 60 liters/minute air sparging and constant pH control at pH 7.0.

Before the batch was inactivated, the culture was plated on Mueller-Hinton agar plates, yeast extract dextrose plates and rabbit blood agar plates at 37° C. and tested for agglutination with *N. meningitidis* group B antiserum. The growth on Mueller-Hinton agar plates, yeast extract dextrose and rabbit blood agar plates was normal and the agglutination reaction was positive. For this batch, the final O.D. was 2.24 thirteen hours after inoculation.

3. Complete Medium for Nephelometer flasks and 70- and 800-liter fermenters

Fraction A

L-glutamic acid: 1.5 g/liter

NaCl: 6.0 g/liter $Na_2HPO_4$.anhydrous: 2.5 g/liter $NH_4Cl$: 1.25 g/liter

KCl: 0.09 g/liter

L-cysteine HCl: 0.02 g/liter

Fraction B (Gotschlich's yeast dialysate)

1280 gm of Difco Yeast Extract were dissolved in 6.4 liters of distilled water. The solution was dialyzed in 2 Amicon DC-30 hollow fiber dialysis units with three H10SM cartridges. The dialysate and 384 gm $MgSO_4.7H_2O$ and 3200 gm dextrose were dissolved in the dialysate and the total volume brought up to 15 liters with distilled water. The pH was adjusted to 7.4 with NaOH and sterilized by filtration through Millipore (0.22 $\mu$) and added to the fermenter containing Fraction A.

For the Nephleometer flasks: 1 liter of Fraction A and 25 ml of Fraction B were added and the pH was adjusted to 7.0–7.2 with NaOH.

For the 70-liter fermenter: 41.8 liters of Fraction A and 900 ml of Fraction B were added and the pH was adjusted to 7.0–7.2 with NaOH.

For the 800-liter fermenter: 553 liters of Fraction A and 15.0 liters of Fraction B were added and the pH was adjusted to 7.0–7.2 with NaOH.

d. Harvest and Inactivation: After the fermentation was completed, phenol (0.5% v/v final concentration) was added to a separate vessel, to which the cell broth was then transferred. The material was held at room temperature with gentle stirring until the culture was no longer viable (about 24 hours).

e. Centrifugation:

After about 24 hours at 4° C., the 614.4 liters of inactivated culture fluid was centrifuged through Sharples centrifuges. The weight of the cell paste after phenol addition was 3.875 kg.

B. Isolation

Step 1. Washing of Bacterial Cells

For each isolation, a two hundred gram aliquot of the above 0.5% phenol-inactivated paste was suspended in a 800 ml portion of sterile distilled water and stirred magnetically to granular suspensions. The suspended cells were peleted at 20,000 xg for 60 minutes at 5° C. (Beckman 19 Ti rotor, 14,500 rpm).

Step 2. Extraction

The washed cells were suspended in 2000 ml of 0.1M Tris-0.01M EDTA Buffer pH 8.5 with 0.5% sodium deoxycholate (TED Buffer) with a Sorvall 2 quart omnimixer at setting 3 for 60 seconds. The homogeneous suspension was tranferred to 16 Erlenmeyer 500 ml flasks for extraction at 56° C. in a shaking waterbath for 15 minutes (at temperature).

The extract was centrifuged at 20,000 xg for 60 minutes at 5° C. (Beckman 19 Ti rotor, 14,500 rpm). The viscous supernatant fluids were then decanted (total volume =1980 ml) and stored at 4° C.

The extracted cell pellets were resuspended in 2000 ml TED Buffer as described immediately above. The suspension was extracted for 15 minutes at 56° C. and centrifuged as above. The supernatant fluids were decanted (volume =2100 ml) and stored at 4° C.

Step 3. Concentration by Ultrafiltration

The extraction supernatants from Step 2 were pooled (total volume =4005 ml). Two liters of the pool were dispensed into a 2 liter New Brunswick fermentation vessel attached to a Millipore Pellicon filter apparatus fitted with two 0.45 micron durapore membranes (½ sq. ft. surface area). The extract supernatant was held at 25° C. in the fermentation vessel throughout the 90-minute concentration process. The sample was concentrated tenfold at an average transmembrane pressure of 27.5 psi.

Step 4. Collection and Washing of the Serotype Protein

The retentate from Step 3 (205 ml) was centrifuged to pellet the serotype protein at 160,000 xg for 2 hours at 5° C. (Beckman 45 Ti rotor, 37,000 rpm). The supernatants were decanted and discarded.

The protein pellets were weighed (8.12 grams) and then suspended in TED Buffer (190 ml buffer; 20 ml/gram pellet) manually with a glass rod and a Dounce homogenizer. The suspension was extracted at 56° C. for 15 minutes (at temperature) in a 500 ml Erlenmeyer flask with shaking. The suspension was centrifuged at 160,000 xg for 2 hours at 5° C. (Beckman 45 Ti rotor, 37,000 rpm). The supernatant fluid was decanted and discarded (volume =190 ml). The pellets were washed a second time in 190 ml of TED Buffer, as above.

Step 5. Recovery of Product

The washed protein pellets from Step 4 were suspended in 100 ml distilled water with a glass rod and a Dounce homogenizer to insure complete suspension. A Lowry Protein value of 17.0 mg/ml was obtained for this suspension. At this point. 200 mg of the suspension were reserved for experimental use. The remaining bulk suspension (91 ml) was diluted to 8.0 mg/ml with 102.4 ml glass distilled water. The aqueous suspension was centrifuged at 12,000 xg for 15 minutes to clear it of aggregates (Beckman 45 Ti rotor, 10,000 rpm).

The supernatant product was withdrawn carefully by pipet to avoid the soft aggregate pellet. The product was labeled (volume =182.5 ml) and aliquots were assayed for sterility and pyrogen (sterile product; no pyrogens). The product was stored at 4° C. as a sterile bulk until use in conjugation at which time it was analytically characterized. The Yield was 9.5 mg Lowry Protein/gram of original cell paste.

TABLE 2-1

| MENINGOCOCCAL B SEROTYPE 2 PROTEIN SOLUTION CHEMICAL ASSAY DATA | |
|---|---|
| Assay | Result |
| Protein Lowry | 4.1 mg/ml |
| Nucleic Acid* | |
| RNA (Bial) | 1.8% |

TABLE 2-1-continued

| MENINGOCOCCAL B SEROTYPE 2 PROTEIN SOLUTION CHEMICAL ASSAY DATA | |
|---|---|
| Assay | Result |
| DNA (Diphenylamine) | 0.6% |
| Neutral Sugars* Anthrone | 1.05 |
| Sialic Acid* | 3.0% |
| Molecular Weight SDS-PAGE | 40,000 d |

*Calculated as percent of Lowry protein.

The following procedures were used in performing the assays:

1. Protein—as in Example 1.
2. Nucleic Acid—Color development was observed with the orcinol reaction (Bial) which corresponded to 1.8% RNA calculated as a percentage of the protein concentration. The diphenylamine test for DNA indicated a 0.6% DNA content calculated as a percentage of the protein in the bulk solution.
3. Neutral Sugars—The neutral sugar content calculated as a percentage of protein was found using the anthrone colorimetric test. (Scott and Melvin, Anal. Chem. 25, 1656, 1953).
4. Sialic Acid—The sialic acid content was found using the resorcinol-HCl method (Svennerholm, Biochem. Biophys., Acta 24, 604, 1957).
5. Molecular Weight—The molecular weight of the mercaptoethanol denatured protein as determined by SDS polyacrylamide gel electrophoresis (Nature 227:680 (1970), LKB Application Note 306).

EXAMPLE 3

PREPARATION OF *H. influenzae* TYPE b POLYSACCHARIDE -*N. Meningitidis* B SEROTYPE OUTER MEMBRANE PROTEIN CONJUGATE I. Preparation of Dowex 50X8 (200–400 mesh) in the tetra-n-butylammonium form 360 ml of fresh Dowex 50X8 (200–400 mesh) strong acid cation exchange resin (Bio-Rad) was charged to a sterile chromatography column and washed with 1500 ml of sterilized, distilled (sd) water and soaked overnight in 800 ml of sd water. The resin was then sequentially washed with one liter of 60:40-sd water:methanol, one liter 40:60-sd water:methanol, and one liter of sd water. The resin was then sterilized by soaking in 650 ml of 3N hydrochloric acid (200 ml HCl, diluted to 800 ml with water). This acid-form resin was aged 19.5 hours and then washed free of excess acid with H2O.

To this column was then added 700 ml of a 1:1 mixture of water:40% tetrabutylammonium hydroxide, which was percolated through the resin until the effluent was basic (pH~10). The resin was washed free of excess base with approximately 2 liters of water and then transferred to a sterile jar. The final effluent was sterile and pyrogen free.

II. Preparation of the tetra-n-butylammonium salt of *H. influenzae* type b polysaccharide(HIb)

A 250 ml round bottom flask fitted with a magnetic stirrer was charged with 3.29 g of HIb and 84 ml of water. The mixture was stirred for 20 minutes and then an additional 15 ml of water was added. Stirring was continued for an additional 30 minutes until all HIb was in solution. The HIb solution was then applied to 150 ml of Dowex 50×8 (200-400 mesh, tetrabutyl ammonium form) in a 45 mm×270 mm column. Ten ml of water was used as a rinse. The column was topped with water and pressure was applied with a hand pump (through a Millex FG, 0.22 μ filter).

Fifty ml fractions were collected in sterile Nalgene centrifuge tubes (50 ml) and each tube was assayed for organic material by applying an approximately 10 μaliquot, using a sterile melting point capillary, to a silica gel plate. The plate was sprayed with a CeIV $(SO_4)_2$/H$_2SO_4$ solution (1% CeIV $(SO_4)_2$ in 10% aqueous sulfuric acid), heated on a hot plate and the "organic" aliquots were detected as black spots. A total of 190 ml from tubes 2, 3, 4, and 5 were combined in a sterile 250 ml centrifuge tube, mixed and then subdivided equally among six tared 250 ml round bottom flasks, labeled A through F. An aliquot was tested and found to be sterile and pyrogen free.

The contents of the six flasks were frozen in dry ice-acetone, appended to two portable 3 outlet vacuum manifolds and lyophilized. The vacuum manifolds were removed to the laminar flow hood and the flasks removed and sealed in sterilized paper bags. These were stored in a dessicator over $P_2O_5$ under high vacuum and at $-20°$ C. A dry sample had the same $K_d$ as the starting HIb.

III. Preparation of Polysaccharide-Butanediamine Adduct (HIb-BuA$_2$)

Step A: Preparation of the 1,4-butanediamine solution 1.46 grams of 1,4-butanediamine dihydrochloride was charged to a 100 ml round bottom flask and dissolved in 58 ml water. 5.0 ml of 2.5N NaOH was added, adjusting the pH to 10.35. The solution was filtered through a 0.22 μ Sybron-Nalge filter and set aside.

Step B: Activation of HIb and reaction with 1,4-butanediamine

To flask A (from section II) containing 0.64 g of the tetra-n-butyl ammonium salt of PRP was added a magnetic stir bar and 17.5 ml of dimethylformamide. The mixture was stirred at room temperature for 25 minutes at which point almost all the material appeared to be in solution.

80 mg of carbonyl diimidazole was weighed into a sterile 6 ml serum vial and then added in one portion to the DMF solution. The flask was capped and the solution was stirred at room temperature for 35 minutes. During this time, 32 ml of the butane diamine solution prepared in A was charged to a 100 ml round bottom flask containing a magnetic stir bar and stirred in an ice bath for about 5 minutes.

After the 35 minute stir time, the DMF solution was added, with a pipet, to the cold 1,4-butane diamine solution. Stirring in the ice bath was continued for 15 minutes, at which time the ice bath was removed, and stirring continued for an additional 17 minutes.

Step C: Dialysis and Lyophilization

The solution was then transferred to autoclaved Spectropor 2 dialysis tubing (cyl. vol. 0.21 ml/mm; 17 inches), and was dialyzed in a 4° C. room. First, the solution was dialyzed vs. 8 liters of 0.01M phosphate buffer at pH 7.0 for 5 hours, then dialyzed twice vs. a fresh 8 liters of phosphate buffer, first for 5 hours, then for 11 hours. Finally, the solution was dialyzed vs. 18 liters of water for 6 hours.

The dialysate (ca. 125 ml) was subdivided into two 250 ml round bottom flasks after an aliquot was taken for sterility and pyrogen testing (results: sterile and pyrogen free). The contents of these flasks were frozen in dry-ice acetone and lyophilized by the method of Section II above. A total of 480 mg was obtained.

The fluorescamine assay indicated 468 nmoles of NH$_2$/mg.

IV. Preparation of Polysaccharide-Butanediamine-Bromoacetamide (HIb-BuA$_2$-BrAc)

Step A: Preparation of p-nitrophenyl bromoacetate 6.30 grams (45 mmole) of bromoacetic acid and 6.25 g (45 mmole) of p-nitrophenol were charged to a 250 ml round bottom flask and dissolved in 50 ml methylene dichloride (CH$_2$Cl$_2$). The solution was stirred in an ice bath for 10 minutes and then 10.3 g (50 mmole) of dicyclohexylcarbodiimide, dissolved in 10 ml of CH$_2$Cl$_2$, was added to it. The reaction mixture was then stirred at 4° C. for 17.25 hours.

The precipitated dicyclohexylurea was then filtered and the filtrate concentrated to dryness in vacuo. The yellow residue was added to 35 ml of 1-chlorobutane, then recrystallized, affording 6.5 g of product, m.p. 85°-87° C., and this product was added to 100 ml of cyclohexane, then recrystallized yielding 4.59 g p-nitrophenyl bromoacetate, m.p. 86°-87° C. Calculations for $C_8H_6NO_4Br$ were C., 36.92; H, 2.30; N, 5.38; Br, 30.77 Found: C., 37.66; H, 2.48; N, 5.28; Br, 30,57.

The $^1$H NMR spectrum was in accord.

Step B. Reaction of HIb-BuA$_2$ 380 mg of HIb-BuA$_2$, prepared in section III above (from 2 flasks), was dissolved in 37 ml of a pH 9.15 buffer in a 250 ml round bottom flask with a magnetic stir bar. To this solution was added 346 mg of p-nitrophenyl bromoacetate (from Step A above) in 9 ml of acetonitrile and the mixture was stirred at 4° C. for 24 hours, then transferred to 18" of dialysis tubing (Spectropor 2, see Section III). This solution was then dialyzed vs. 18 liters of water for 5.25 hours and then vs. a fresh 18 liters of water for 17.25 hours (both a 4° C.).

The 100 ml of dialysate was sequentially filtered through a 0.45 μ Sybron Nalge filter and a 0.20 μ filter. Then it was divided equally into six 100 ml round bottom flasks, then frozen and lyophilized as in section II. A total of 0.28 g of HIb-BuA$_2$-BrAc was obtained. The fluorescamine assay indicates 128 nmoles NH$_2$/mg, resulting in 340 nmoles bromoacetyl groups/mg by difference. The rate nephelometry assay indicates the same antigenicity as the starting polysaccharide.

V. Conjugation of HIb-BuA$_2$-BrAc to Functionalized *N. Meningitidis* membrane protein (NMP)

Step A. Functionalization of NMP with N-acetyl homocysteine thiolactone

To a 6 ml serum vial containing 42 mg ethylene diamine tetracetic acid and 8 mg dithiothreitol, was added 5 ml of pH 11.3 borate buffer. 3.8 ml of the above solution was charged to a 50 ml round bottom flask and 11.5 ml of a solution of *Neisseria meningitidis* outer membrane protein (NMP) was added. The pH of the resulting mixture was adjusted to 11.39 with 40–50 μl of 2.5N NaOH.

The flask was capped with a mushroom type serum stopper and the air replaced by nitrogen using a Firestone valve (ACE Glass Co.). 53 mg of N-acetyl-homocysteine thiolactone was added in a nitrogen box, and the resultant solution was aged in the $N_2$ atmosphere at room temperature for 16.7 hours. This solution was then applied to a column containing 120 ml of Sephadex G25 (fine), which was operated in the nitrogen box. Elution was with pH 8 phosphate buffer and 5 ml fractions were collected and assayed by the Ellman test for thiols. Baseline separation of high molecular weight (i.e., protein) thiol from lower molecular weight material was effected.

Step B. Conjugation

The high molecular weight fractions were combined and added to one of the 50 ml flasks containing 0.06 g of HIb-BuA$_2$-BrAc (section IV). This solution was aged in the N$_2$ box at room temperature for 6 hours and charged to a sterile Spectropor dialysis tubing and dialyzed at 4° C. vs. 18 liters of water for 15 hours, then dialyzed vs. a fresh 18 liters of water for 24 hours.

Step C. Centrifugation

The dialysate (approximately 32 ml) was transferred with a pipet in 25 ml and 7 ml fractions to two polycarbonate centrifuge tubes and centrifuged at 4° C. for 2 hours at 37,000 rpm (100,000 xg) in a Beckman Ti 60 rotor. The supernatant fluids were decanted and the pellets were transferred to a Dounce homogenizer with about 8 ml of water, homogenized and returned to one of the centrifuge tubes. This tube was filled to 25 ml with water, effecting a complete resuspension, and the tube was recentrifuged at 37,000 rpm, (100,000 xg) at 4° C. for 2 hours. The second supernatants were decanted and the pellets Dounce-homogenized in 8 ml of water. The homogenate was transferred to a sterile 15 ml nalge centrifuge tube and diluted to 15 ml with water.

After aging at 4° C. overnight, a small amount of flocculent solid appeared and this was removed by a short (5 min.) spin in a clinical centrifuge at about 2500 rpm.

The above activation, conjugation and centrifugation procedures were repeated twice in like manner. They were analyzed for protein, and polysaccharide content, S-carboxymethylhomocysteine (SCMHC), lysine ratio, sterility and pyrogenicity. All samples were sterile and pyrogen free. The other results are presented in the Table below.

| Run | Polysaccharide μg/ml | Protein μg/ml | Ratio | SCMHC/lysine |
|---|---|---|---|---|
| 1 | 105 | 1210 | .09 | .011 |
| 2 | 154 | 1700 | .09 | .019 |
| 3 | 166 | 1800 | .09 | .027 |

The consistency of the ratio of polysaccharide to protein which characterizes the conjugate confirms the reproducibility of the process, and the ratio of S-carboxymethylhomocysteine to lysine is an indication of the reaction efficiency, with a result greater than 0 proving the covalency of the bond between the covalently-modified polysaccharides and proteins.

The solutions were combined for the clinical lot and lyophilized in the presence of lactose (20 μg/ml polysaccharide/4 mg/ml lactose).

EXAMPLE 4

PREPARATION OF H. influenzae TYPE b POLYSACCHARIDE-N. MENINGITIDIS B SEROTYPE OUTER MEMBRANE PROTEIN CONJUGATE "CAPPED" WITHIN N-ACETYLCYSTEAMINE The preparation of functionalized polysaccharide, HIb-BuA$_2$-BrAc, is the same as in Example 3 (Sections I through IV). The preparation of functionalized NMP is the same as in Example 8 (for the preparation of Step B (III)-NMP conjugate) Section IVA.

To a flask containing 4 ml of thiolated protein (5.6μ moles SH by Ellman assay) was added 59 mg of HIb-BuA$_2$-BrAc (300 nanomoles bromoacetyl by difference). The flask was sealed with a septum, degassed, with the air being replaced by nitrogen, and the solution was aged for 18.5 hours. 6 ml of water was added and the solution was transferred to a 10 ml polycarbonate centrifuge tube and centrifuged for 2 hours at 43,000 rpm in a Beckman 75 Ti rotor at 4° C. The supernatant was removed and the pellet was resuspended with a Dounce homogenizer in 10 ml of a pH8, 0.1M phosphate buffer containing 106 mg of N-acetylcysteamine, the solution was degassed and aged at room temperature for 19.5 hours.

It was then centrifuged as above (43,000 rpm, 4° C., 2 hours, 75 Ti rotor). The pellet was suspended (without homogenization) in 9.7 ml of water and recentrifuged as above. The resultant pellet was resuspended with homogenization in 25 ml of water and then diluted to 30 ml with water affording an aqueous suspension of the "capped" product.

The analysis of the conjugate was:

| Polysaccharide Concentration | Protein Concentration | HIB/Protein Concentration |
|---|---|---|
| 188 μg/ml | 1200 μg/ml | 0.157 |

Spinco: SCMHC/lysine = 0.096
S—carboxymethylcysteamine/lysine = 0.20

EXAMPLE 5

ANTIBODY RESPONSE TESETS IN ANIMALS WITH H. influenzae TYPE b POLYSACCHARIDE-N. meningitidis B. SEROTYPE OUTER MEMBRANE PROTEIN CONJUGATE An H. influenzae type b polysaccharide-N. meningitidis B serotype outer membrane protein conjugate prepared lyophilized according to the procedue of Example 3 was tested for immunogenic response in ICR/Ha mic and Rhesus monkeys of various ages, and the results were tabulated in Tables 2 and 3.

The analysis of the conjugate was:

| Polysaccharide Concentration | Protein Concentration | Ps/Protein Ratio | Yield Ps |
|---|---|---|---|
| 276 μg/ml | 2.38 mg/ml | 0.12 | 6.1% |

TABLE 5-1

Serum Antibody Response of ICR/Ha Mice at Various Ages Immunized with H. influenzae type b Polysaccharide-Protein Conjugates

| | RIA Titer (GMT) ng ab/ml Mouse age, days* | | | |
|---|---|---|---|---|
| Sample | 7 | 21 | 28 | 35 |
| H. flu polysaccharide-protein conjugates | 282** 201** | 2111 | 8645 | 15860 |

*age at the time of the first in action; mice injected s.c. with 2 μg/0.1 ml on days 0, 14; bled day 21.
**separate litter; 7-8 mice in all groups.

The potency of the H. influenzae type b polysaccharide conjugate was tested in mice and the results shown in Table 2. The conjugate proved to be highly immunogenic.

TABLE 5-2

Thymic Dependency Studies in Nude (Athymic) Mice Immunized with *H. influenzae* type b Polysaccharide-Protein Conjugates

| Sample | Dose g Polysaccharide | RIA Titer (GMT) ng ab/ml | |
|---|---|---|---|
| | | Nu/Nu Mice* | Nu/+ Mice* |
| H. flu polysaccharide- | (1) 2.5 | 1,802 | 11,362 |
| protein conjugates | (2) | 1,304 | 8,712 |
| Saline control | (1) — | — | 50 |
| | (2) | | 55 |

*mice injected subcutaneously on days 0, 14; bled on day 21.

The response in Nu/Nu mice avereaged about 15% of the response in Nu/+mice, indicating that the conjugate was a thymus-dependent antigen.

TABLE 5-3

Serum Antibody Response of Rhesus Monkeys Immunized with *H. influenzae* type b Polysaccharide-Protein Conjugates

| Rhesus Monkey Age* | Dose Polysaccharide | RIA Titer (GMT) ng ab/ml days | | | |
|---|---|---|---|---|---|
| | | 0 | 14 | 28 | 42 |
| 2-3 months | 20 μg | 50 | 116 | 195 | 3036 |
| 4 months | 20 μg | 50 | 414 | 437 | 1548 |
| 18 months | 20 μg | 124 | 5858 | 4785 | 7447 |

*Three monkeys per group.

As shown in Table 2, the *H. influenzae* type b polysaccharide conjugate induced a high immunogenic response is Rhesus monkeys of various ages, also.

EXAMPLE 6

THE CONJUGATION OF PNEUMOCOCCAL POLYSACCHARIDE TYPE 19F AND OUTER MEMBRANE PROTEIN OF *neisseria meningitidis*:

I: Preparation of the tetra-n-butylammonium salt of Pneumococcal Type 19F polysaccharide.

A 25 ml round bottom flask fitted with a magnetic stirrer was charged with 50 mg of polysaccharide type 19F (Merck) and 5 ml of $H_2O$, and the mixture was stirred for 20 minutes. The solution was then applied to a 3 ml column of Dowex 50×8 (200-400 mesh, tetrabutylammonium form), eluted with water, and collected in a 25 ml Erlenmeyer flask.

The solution was assayed for polysaccharide content on silica gel plates sprayed with $CeIV(SO_4)/H_2SO_4$ solution, then heated on a hot plate, resulting in the aliquots containing polysaccharide being detectable as black spots. The solution containing polysaccharide 19F was freeze dried and 52 mg was recovered.

II. Reaction of the tetrabutylammonium salt of pneumococcal type 19F with carbonyldiimidazole followed by reaction with 1,4-butanediamine (19F-$BuA_2$).

Step A: Preparation of the 1,4-butanediamine solution 40 mg of 1,4-butanediamine dihydrochloride was dissolved in 1.0 ml of $H_2O$ and adjusted to pH 9.15 with 2.5N NaOH.

Step B: Activation of type 19F polysaccharide and reaction with 1,4-butanediamine To a 25 ml round bottom flask containing 20 mg of type 19F polysaccharide in the tetrabutylammonium form, was added a magnetic stir bar and 4 ml of dimethyl sulfoxide (DMSO). The mixture was stirred at room temperature for 20 minutes at which point all material was in solution. 5 mg of carbonyldiimidazole was added and the reaction was stirred for 30 minutes at room temperature. During this time, the 1,4-butanediamine solution prepared in Step A was charged to a 25 ml round bottom flask with a magnetic stir bar and stirred in an ice bath for about 5 minutes. After the 30 minutes stir time, the DMSO solution was added, with a pipet, to the cold 1,4-butanediamine solution. Stirring in the ice bath was continued for 15 minutes, at which time the ice bath was removed, but stirring was continued for an additional 15 minutes at room temperature.

Step C: Dialysis and Lyophilization

The solution was then transferred to Spectropor 2 dialysis tubing and dialyzed in a 4° C. room with stirring. The solution was first dialyzed vs. 4 liters of 0.01M phosphate buffer at pH 7.0 for 8 hours, then dialyzed vs. 4 liters of 0.01M phosphate buffer at pH 7.0 for 8 hours. Finally, the solution was dialyzed vs 4 liters of water for 6 hours. The solution was then lyophilized and 19 mg of the butanediamine derivative of type 19F polysaccharide (19F-$BuA_2$) was recovered. Fluorescamine assay indicated 100 nanomoles of $NH_2$/mg of material.

III. Reaction of 19F-$BuA_2$ with p-nitrophenyl bromoacetate

Step A: Reaction of 19F-$BuA_2$ 15 mg of 19F-$BuA_2$, prepared in II above was suspended in 2 ml of pH 9.15 buffer in a 25 ml round bottom flask with a magnetic stir bar and stirred for 10 minutes until all material had gone into solution. To this solution was added 15 mg of p-nitrophenyl bromoacetate dissolved in 0.2 ml of acetonitrile. The mixture was stirred at 4° C. for 24 hours and transferred to Spectropor 2 dialysis tubing. This was dialyzed twice against 4 liters of $H_2O$. The sample was freeze dried and 9 mg of the N-bromoacetylated derivative of 19F-$BuA_2$ (19F-$BuA_2$-BrAc) was obtained.

Fluorescamine assay indicated 57 nanomoles $NH_2$/mg, resulting in 43 nanomoles of bromoacetyl groups/mg, by difference.

IV. Conjugation of 19F-$BuA_2$BrAc to Functionalized Outer membrane protein of *neisseria meningitidis* (NMP)

Step A: Functionalization of NMP with N-acetylhomocystein thiolactone 43 mg of ethylenediamine tetraacetic acid and 8 mg of dithiothreitol were dissolved in 5 ml of saturated borate buffer, pH 11.30. 0.4 ml of the above solution was charged to a 15 ml centrifuge tube and 1 ml (13.7 mg) of a solution of *neisseria meningitidis* outer membrane protein (NMP) was added. The solution was degassed and placed under $N_2$ atmosphere at room temperature for 16 hours. The solution was then diluted to a total volume of 2.5 ml, by adding 1.1 ml of pH 8.0 phosphate buffer. This solution was then applied to a PD10 column (Sephadex G25M), which had been pre-equilibrated under $N_2$ with pH 8.0 phosphate buffer. The sample was eluted with 3.5 ml of pH 8.0 phosphate buffer. Thiol content was determined by the Ellman assay and found to be 1.89 μ moles/sample. 2.5 ml of the sample were applied to a second PD10 column also preequilibrated with pH 8.0 phosphate buffer. It was eluted with 3.5 ml of pH 8.0 phosphate buffer. Thiol content by Ellman assay was 0.44 μmoles/sample.

Step B: Conjugation

To the 15 ml pyrex centrifuge tube containing the protein solution was added 9 mg of 19F-$BuA_2$-BrAc from III above. This solution was aged in a $N_2$ glove box at room temperature for 6 hours. It was then charged to Spectropor 2 dialysis tubing and dialyzed at 4° C. vs. 4 liters $H_2O$ for 8 hours and then again vs. 4 liters H2O for 8 hours. An aliquot was freeze dried for amino acid analysis.

Found: lys 0.141μ moles/mg SCMHC. 0.0062 μmoles/mg, with this value greater than 0 proving covalency.

Step C: Centrifugation

The dialysate (approximately 10 ml) was transferred with a pipet to a polycarbonate centrifuge tube and centrifuged at 4° C. for 2 hours at 37,000 RPM (100,000 xg) in a Beckman Ti60 rotor. The supernatants were poured off and the pellets were transferred to a homogenizer with about 2 ml of H2O, where it was homogenized and returned to one of the centrifuge tubes. This was filled to 10 ml with H2O and recentrifuged at 37,000 RPM (100,000 xg) at 4° C. for 2 hours. The second supernatant was poured off and the pellet homogenized in 8 ml of H2O. The homogenate was stored in a plastic 15 ml centrifuge tube and tested for immunogenicity.

TABLE 6-1

Serum Antibody Response of ICR/Ha Mice Immunized with Pneumococcal 19F-Meningococcal B Serotype Outer Membrane Protein Conjugate

| Sample | Dose μg Polysaccharide | RIA Titer (GMT) ng ab/ml* |
| --- | --- | --- |
| Ps19F-Pro conjugate | 0.5 | 17,338 |

*Mice injected i.p. on days 0, 7, 28; bled on day 35.

As shown in Table 6-1, the conjugate proved to be highly immunogenic.

EXAMPLE 7

THE CONJUGATION OF PNEUMOCOCCAL POLYSACCHARIDE TYPE 19F AND THRICE-PURIFIED HEMP SEED GLOBULIN (EDESTIN)

I: Preparation of the tetra-n-butylammonium salt of Pneumococcal Type 19F polysaccharide.

A 50 ml round bottom flask fitted with a magnetic stir bar was charged with 105 mg of polysaccharide type 19F (Merck) and 6 ml of water. The mixture was stirred for 20 minutes and the solution applied to a 6 ml column of Dowex 50×8 (200–400 mesh, tetra-n-butylammonium form). The column was eluted with water and the eluant was collected in a 50 ml Erlenmeyer flask. The eluant was assayed for polysaccharide content on silica gel plates, sprayed with CeIV ) (SO4)2/H2SO4 solution and then heated on a hot plate. The aliquots containing polysaccharide were detected as black spots. The solution containing polysaccharide 19F was freeze dried and 112 mg of the tetra-n-butylammonium salt of 19F was recovered.

II: Reaction of the tetra-n-butylammonium salt of Pneumococcal type 19F with carbonyldiimidazole followed by reaction with 1,4-butanediamine Step A: Preparation of the 1,4-butanediamine solution 175 mg of 1,4-butanediamine dihydrochloride was dissolved in 7 ml of H20 and the pH of the solution was adjusted to 9.5 with 2.5N NaOH.

Step B: Activation of type 19F polysaccharide and reaction with 1,4-butanediamine To a 50 ml round bottom flask containing 112 mg of type 19F polysaccharide in the tetrabutylammonium form was added a magnetic stir bar and 5 ml of dimethyl sulfoxide (DMSO). The mixture was stirred at room temperature for 10 minutes at which point all material was in solution. 13 mg of carbonyldiimidazole was added and the reaction was stirred for 35 minutes at room temperature. During this time the 1,4-butanediamine solution prepared in Step A above was charged into a 50 ml round bottom flask having a magnetic stir bar and sitting in an ice bath and the solution was stirred for about 5 minutes. After the 35 minute stirring time, the DMSO solution was added, with a pipet, to the cold 1,4-butanediamine solution. Stirring was continued for 15 minutes, at which time the ice bath was removed, and resumed for an additional 15 minutes with the solution at room temperature.

Step C: Dialysis and Lyophilization

The solution was then dialyzed in Spectropor 2 dialysis tubing at 4° C. with stirring. The solution was first dialyzed vs. 4 liters of 0.01M phosphate buffer at 7.0 pH for 8 hours, then dialyzed vs. 4 liters of 0.01M phosphate buffer at 7.0 pH for 8 hours. Finally, the solution was dialyzed vs. 4 liters of water for 4 hours. The solution was then lyophilized and 80 mg of the butanediamine derivative of type 19F polysaccharide (19F-BuA2) was recovered. Fluorescamine assay indicated 77 nanomoles of NH2/mg.

III. Reaction of 19F BuA2 with p-nitrophenyl bromoacetate.

Step A: Reaction of 19F-BuA2

50 Mg of 19F-BuA2 prepared in Section II above was suspended in 4 ml of pH 9.15 buffer in a 25 ml round bottom flask with a magnetic stir bar and stirred for 10 minutes until all material was in solution. To this solution was added 50 mg of p-nitrophenyl bromoacetate dissolved in 0.5 ml of acetonitrile. The mixture was stirred at 4° C. for 24 hours and then transferred to Spectropor 2 dialysis tubing. This was dialyzed twice against 4 liters of water. The sample was then freeze dried and 44 mg of the N-bromoacetyl derivative of 19F-BuA2 (19F-BuA2-BrAc) was obtained. Fluorescamine assay indicated 7.5 nanomoles NH2/mg resulting in 69.5 nanomoles bromoacetyl groups/mg by difference.

IV. Conjugation of 19F-BuA2-BrAc to functionalized and purified Hemp Seed Globulin (Edestin).

Step A: Purification of Edestin by high performance liquid chromatograhy (HPLC)

240 mg of twice crystallized edestin from hemp seed (Sigma) was dissolved in 4 ml of 3M guanidine, pH 7.0. The sample was shaken vigorously and 0.1 ml of mercaptoethanol was added. Upon shaking, a great deal of foam was formed.

The sample was allowed to stand at room temperature for one hour and centrifuged in a table top centrifuge to remove the foam and filtered thru a Millex-GV 0.22 micron filter (Millipore). Half of the sample (2 ml, 120 mg) was then injected on to a prep size TSK 3000 molecular sieving column with the following parameters: flow rate: 1 ml/min.; λ max: 280 nm; solvent: 3M guanidine; UV range: 2.0; chart speed: 0.25 cm/min.

The appropriate fractions as detected by UV were collected and dialyzed in Spectropor 2 dialysis tubing against 30 liters of water for 16 hours. Replacement of 3M guanidine with water during dialysis caused precipitation of the purified edestin.

The entire sample was transferred from the dialysis bag to a centrifuge tube and centrifuged in a table top centrifuge for 5 minutes. The pellet which contains the purified edestin was collected and dried under vacuum over P2O5. The other half of the original sample (2 ml, 120 mg) was then injected and carried through identical steps. 110 mg of purified edestin was isolated. The purified edestin was then dissolved in 2.0 ml of 3M guanidine, centrifuged, filtered and rechromatographed two additional times using the same procedure. After three purifications, a total of 18 mg was isolated which was a single peak on an analytical B TSK 3000 column.

Step B: Functionalization of thrice-purified edestin 3 mg of ethylenediamine tetraacetic acid and 5μ of mercaptoethanol were placed in 1 ml of 3M guanidine. To this solution was added 14 mg of thrice-purified edestin prepared in Step A above. The pH of the solution was adjusted to 9.5 with 20 μl of 2.5M NaOH and the solution was degassed and placed under $N_2$. 13 mg of N-acetylhomocysteine thiolactone was added in a nitrogen box, and the resultant solution was aged in the $N_2$ atmosphere at room temperature for 16 hours.

The solution was then diluted to a final volume of 2.5 ml, by adding 1.4 ml of 3M guanidine, and applied to a PD10 column (Sephadex G25M Pharmacia) which had been pre-equilibrated under $N_2$ with 3M guanidine. The sample was eluted with 3.5 ml of 3M guanidine. Thiol content was determined by the Ellman assay and found to be approximately 4.38 μmoles/sample. 2.5 ml of the sample was applied to a second PD10 column, also pre-equilibrated with 3M guanidine then eluted with 3.5 ml of 3M guanidine. Thiol content by Ellman assay was 3.24 μmoles/sample.

Step C: Conjugation

To the centrifuge tube containing the edestin solution was added 7 mg of bromoacetylated type 19F polysaccharide (19F-BuA$_2$-BrAc) (section III). This solution was aged in the $N_2$ box at room temperature for 6 hours. It was then charged to Spectropor 2 dialysis tubing and dialyzed twice, each time vs. 4 liters of water for 8 hours. The entire sample was freeze dried and a small portion was sent for amino acid analysis.

Found: lysine, 0.105 μmoles/mg; SCMHC, 0.003 μmoles/mg, proving covalency of the bond between the modified polysaccharides and proteins.

EXAMPLE 8

PREPARATION OF *streptococcus agalactiae* (STREP B-TYPE III) POLYSACCHARIDE -*n. memingitidis* B SEROTYPE OUTER MEMBRANE PROTEIN CONJUGATE I: Preparation of tetra-n-butylammonium salt of Step B (III)

100 mg of Step B (III) polysaccharide (prepared essentially according to the method of U.S. Pat. No. 4,413,057 to Carlo et al) was dissolved in 4 ml of water and applied to a 7 ml column of Dowex 50×8 (200–400 mesh) cation exchanged resin, tetrabutylammonium form. The column was eluted with water and the fractions (3 ml) were checked for organic material by the CeIV(SO$_4$)$_2$/H$_2$SO$_4$ method. The appropriate fractions were lyophylized and 100 mg of the tetra-n-butylammonium salt of Step B (III) polysaccharide was obtained.

II: Preparation of Polysaccharide - Butanediamine Adduct (Strep B (III)-BuA$_2$)

50 mg of the Strep B (III) tetrabutylammonium salt was suspended in 2.5 ml of dry dimethylformamide (DMF) and stirred for 10 minutes until complete solution was accomplished. 5 mg of 1,1-carbonyldiimidazole was then added in one portion and the solution was stored at room temperature for 35 minutes. This solution was then added to 3 ml of a solution containing 80 mg of 1,4-butanediamine 2HCl whose pH had been adjusted to 10.3 with 2.5N NaOH, and which had been cooled in an ice bath. The resultant mixture was stored in the ice bath for 15 minutes and at room temperature for an additional 15 minutes.

The mixture was then dialyzed vs 4 liters of 0.1M phosphate buffer (pH7) three times for 5 hours, 17 hours and 7 hours, respectively. A final dialysis vs 4 liters of water for 18 hours was followed by lyophilization, which afforded 32 mg of the Step B (III) -butane diamine adduct, Strep 13 (III)-BuA$_2$. The fluorescamine assay indicated 212 nanomoles NH$_2$/mg.

III. Preparation of Polysaccharide-Butanediamine Bromoacetamide (Strep B (III)-BuA$_2$-BrAc)

26.8 mg of Strep B (III)-BuA$_2$ was dissolved in 2.5 ml of pH9 borate buffer and 28 mg of p-nitrophenyl bromoacetate 0.4 ml of acetonitrile was added to the solution. The mixture was stirred at 4° C. for 23.5 hours and then dialyzed at 4° C. vs 30 liters of water for 17 hours and then 4 liters of water for 6 hours. Lyophilization afforded 27 mg of Step B (III)-BuA$_2$-BrAc. Fluorescamine assay indicated 35 nanomoles NH$_2$/mg resulting in 177 mmol/mg bromoacetyl by difference. The material was fully antigenic by rate nephelometry.

IV. Conjugation of Strep B (III)-BuA$_2$-BrAc to Functionalized *N. Meningitidis* Membrane Protein (NMP)

A. Functionalization of NMP: 10 ml of an NMP solution (5 mg/ml) was charged to a polycarbonate antifuge tube and centrifuged at 43,000 r.p.m. for 2 hours at 4° C. in a Beckman 75 Ti rotor. The supernatant was removed and the pellet was resuspended in 4 ml of a pH 11.3 borate buffer containing 33.6 mg of ethyldiamine tetraacetic acid disodium salt, 6.4 mg of dithiothreitol. The resuspension was effected with a Dounce homogenizer. The mixture was charged to a centrifuge tube, capped with a serum cap, degassed and nitrogenated and to this was added 55 mg of N-acetyl homocysteine thiolactone. The resultant mixture was aged under $N_2$ for 18 hours at room temperature. The pH was then adjusted (under $N_2$) to 7.25 with 2.6 ml of 1 M KH$_2$PO$_4$ and 2.6 ml 0.1 M phosphate buffer, and the mixture transferred to a centrifuge tube (under $N_2$). It was then centrifuged as above (2 hours, 4° C., Ti 75 rotor 43,000 rpm). After the supernatant was removed the pellet was resuspended (as above with a Dounce homogenizer) in 10 ml of pH8 0.1 M phosphate buffer. Recentrifugation (as above) of this suspension, followed by resuspension of the pellet in 4 ml of pH8 buffer afforded a solution whose thioltiter indicated a total of 5.6 μmoles SH. A control experiment showed that this is solely due to thiolated protein and small molecules (e.g. hydrolyzed thiolactone) are absent.

B. Conjugation and purification: To the 4 ml of resuspended pellet was added (under $N_2$) 24 ml of Step B (III)-BuA$_2$-BrAc and the mixture aged for 18.75 hours at room temperature under $N_2$. The mixture was transferred to a 10 ml polycarbonate centrifuge tube, and topped with water. After centrifugation (as above), the pellet was resuspended (as above) in 10 ml of water and recentrifuged (as above). The final pellet was resuspended in 15 ml of water (as above) and the suspension had a protein content of 2.7 mg/ml and a polysaccharide content of 0.263 mg/ml.

The SCMHC/lys ratio was 0.044

EXAMPLE 9

PREPARATION OF *escherichia coli* K1 CAPSULAR POLYSACCHARIDE

Inoculum and Seed Development

A lyophilization vial of *Escherichia coli* K1 seed stock (received from Dr. John Robbins, BOB) was thawed and diluted with approximately 1 ml of Trypticase-hysoy-glucose (THG) medium. One Trypticase-soy agar slant was then streaked on the day prior to the fermentation run and incubated overnight at 37° C., at which time growth on the slant was removed and suspended in 1 liter of THG medium.

Trypticase-hysoy-glucose (THG) medium is prepared by autoclaving 9.5 liters of Solution A at 121° C. for 90 minutes, then cooling it and adding to it 500 ml of solution B, which has been autoclaved separately at 121° C. for 30 minutes.

| Solution A | | |
|---|---|---|
| a. Trypticase soy broth (BBL) | 300 | g |
| b. Hysoy (Sheffield) | 100 | g |
| c. Phenol red | 90 | mg |
| d. UCON LB-625 antifoam (Union Carbide) | 10 | ml |
| e. Distilled water sufficient to give of solution | 9.5 | liters |
| Solution B | | |
| a. Dextrose (anhyd.) | 50 | g |
| b. Distilled water sufficient to give of solution | 500 | ml |

Fermentation

The 1 liter of growth THG medium which had been inoculated from the agar slants was grown in a 2-liter Erlenmeyer flask at 37° C. with 200 rpm stirring for 6 hours (when cell growth was observed). This one liter was then inoculated into 10 liters of THG medium in a 14-liter New Brunswick Scientific fermenter in which the air flow was set at 2 liters/minute and the stirrer was set at 200 rpm. The pH was adjusted and maintained at 6.8 to 7.4 with 10% NaOH for 6 hours, when two similar O.D. readings were observed.

Harvest and Clarification

The final fermentation broth from above was then added to a 5-gallon plastic bottle containing hexadecyltrimethylammonium bromide (final concentration 0.3% wt/vol). After 4 hours at 4° C. during which the hexadecyltrimethylammonium bromide-precipitated polysaccharide was allowed to settle out, the broth was sampled for inactivation and when certified, was centrifuged in a laboratory Sharples centrifuge at approximately 30,000 rpm for 20 minutes, and the supernatant was discarded. The cell pellet (approximately 66 g) was saved for isolation purposes.

Suspension and Extraction

Three pellets from three fermentation batches were suspended individually in 400 ml of 1.0M $CaCl_2$ and these suspensions were extracted in an Omni-mixer, submerged in an ice-water bath, for 30 minutes on setting 2, and combined.

25% Ethanol Precipitation to Remove Contaminants 373 ml of absolute ethanol was added dropwise (to a 25% ethanol concentration), with stirring, to the 1130 ml of $CaCl_2$ suspension from the preceding step and the mixture was left overnight at 4° C. The resultant precipitate was removed by centrifugation in a Beckman J-21B centrifuge at 11,000 x G for 30 minutes at 4° C. and discarded.

75% Ethanol Precipitation to Collect Crude Polysaccharide 2560 ml of absolute ethanol was added dropwise (to a 75% final concentration), with stirring, to the 1280 ml of clear supernatant fluid from the preceding precipitation step, and the mixture was allowed to stand overnight at 4° C. to ensure complete precipitation of the crude polysaccharide.

Recovery of the Crude Polysaccharide

The insoluble precipitate was recovered by centrifugation in the Beckman-21B unit at 11,000 x G for 30 minutes, at 4° C., and washed once with about 200 ml of absolute ethanol and once with about 200 ml of acetone, with both washes being discarded. The insoluble product was then dried in vacuo at 4° C. over anhydrous $CaCl_2$ (yield 4.6 g).

Phenol Extraction and Dialysis

The 4.6 g of crude polysaccharide was suspended in 400 ml of 0.488M sodium acetate, pH 6.9, at 11.5 mg/ml, using a Dounce homogenizer, and this solution was extracted three times with separate 200 ml amounts of aqueous phenol solution, prepared by adding 180 ml of 0.488M sodium acetate, pH 6.9, into a one pound bottle of Mallincrodt crystalling phenol until complete solution was effected. Each phenol extract was then centrifuged at 11,000 x G for 30 minutes, at 4° C., to break the emulsion, and the aqueous phases were aspirated, pooled and extracted, with the phenol phases being discarded.

The pooled aqueous phases were dialyzed, at 4° C. for 24 hours, with changes of glass-distilled water such that the final dialysis ratio was greater than 1:100,000.

75% Ethanol Precipitation to Collect the Polysaccharide 7.6 ml of 2M $CaCl_2$ was added to the 305 ml of the dialysate of the above step, to a final concentration of 0.05M $CaCl_2$, and 938 ml of absolute ethanol was added dropwise (to a concentration of 75% ethanol) to the rapidly-stirring solution. After standing overnight at 4° C., the resultant precipitate was collected by centrifugation in the Beckman unit for 30 minutes, at 11,000 x G and 4° C., then washed once with about 200 ml of absolute ethanol, once with about 200 ml of acetone, and dried in vacuo over anhydrous $CaCl_2$ at 4° C. (yield =1.7 g).

Ultracentrifugation

The 1.7 g of polysaccharide was resuspended in 170 ml of 0.05M $CaCl_2$, 18.9 ml of absolute ethanol was added dropwise, with stirring, and the solution was centrifuged at 100,000 x G at 4° C. for 2 hours.

Product Collection

The resulting 180 ml of clear supernatant fluid was removed by decanting and 468 ml of ethanol was added dropwise (to a concentration of 75% ethanol) while stirring, in order to precipitate the polysaccharide. The mixture was left overnight at 4° C. to ensure complete precipitation, the product was collected by centrifugation at 11,000 x G for 30 minutes at 4° C., washed once with 200 ml of absolute ethanol, once with 200 ml of acetone, and dried in vacuo over anhydrous $CaCl_2$ at 4° C. (yield =1.46 g).

Ultracentrifugation

The 1.46 g of polysaccharide was resuspended in 150 ml of 0.05M $CaCl_2$, 50 ml of absolute ethanol was added dropwise (to a 25% concentration) to the rapidly-stirring solution, and the solution was ultracentrifuged, at 100,000 x G and 4° C., for two hours.

Final Product Collection

The resulting 190 ml of clear supernatant fluid was removed from the pellet by decanting and 190 ml of ethanol was added dropwise (to a concentration of 50%), while stirring. The mixture was allowed to stand for two days at 4° C. to ensure complete precipitation and the final product was collected by centrifugation in the Beckman J-21B centrifuge at 11,000 x G for 30 minutes at 4° C. Finally, the product was washed once with about 200 ml of ethanol, once with about 200 ml of acetone, and dried in vacuo over anhydrous $CaCl_2$ at 4° C. (yield =1.2 g).

EXAMPLE 10

PREPARATION OF *e. coli* Kl CAPSULAR POLYSACCHARIDE-*n. meningitidis* B-SEROTYPE OUTER MEMBRANE PROTEIN CONJUGATE I. Preparation of tetra-n-butylammonium salt of *E. coli* Kl polysaccharide:

103 mg of *E. coli* Kl polysaccharide (prepared according to the method of Example 9) was dissolved in 2 ml of water and the solution applied to a 4 ml column of Dowex 50×8 (200–400 mesh, tetra-n-butylammonium form). The column was eluted with water and the fractions (3 ml) were checked for organic material by the Ce(IV) $So_4)_2/H_2SO_4$ method. The appropriate fractions were lyophilized and the product dried in a dessicator over $P_2O_5$, affording 134 mg of the tetrabutylammonium salt a similar previous preparation was analyzed by 'HNMR and appeared to have roughly stoichiometric amounts of tetra-n-butylammonium ion.

II. Preparation of Polysaccharide-Butanediamine Adduct (*E. coli* Kl-$BuA_2$)

The 134 mg of the salt prepared in I was dissolved in 3 ml dry, degassed dimethytformamide and stirred for 12 minutes. 12.7 mg of 1,1-carbonyl diimidazole were then added in one portion and the solution stirred for 30 minutes. Then the solution was added to 6 ml of an ice cooled aqueous solution containing 145 mg 1,4-butanediamine 2HCl whose pH had been adjusted to 10.35 with 2.5N NaOH. This solution was stirred for 15 minutes in the ice bath and for 20 mintues at room temperature. It was then dialyzed three times vs 4L of 0.1 M phosphate buffer (pH7) for 5.5 hours, 16 hours and 3.75 hours respectively. A final dialysis vs 4L of $H_2O$ was effected for 4.5 hours. Lyophilization afforded 73 mg of *E. coli* Kl-$BuA_2$. Fluorescamine assay indicated 180 nanomoles $NH_2$/mg.

III. Preparation of Polysaccharide-butane diamine-bromoacetamide (*E. coli* $K_1$-$BuA_2$-BrAc)

68 mg of *E. coli* Kl-$BuA_2$ was dissolved in 6.7 ml of pH9 borate buffer and 70 mg of p-nitrophenyl bromoacetate in 1.5 ml of acetonitrile were added. The mixture was stored for 19 hours at 4° C. and then dialyzed vs 32 liters of $H_2O$ and 4 liters of water for 8 hours and 13 hours respectively. The solution was lyophilized to 74 mg of *E. coli* Kl-$BuA_2$-BrAc. Fluorescamine assay indicated 50 nanomoles of $NH_2$/mg resulting in 120 nanomoles of bromoacetyl/mg by difference.

IV. Conjugation of *E. coli* Kl-$BuA_2$-BrAc to Functionalized *N. meningitidis* Membrane Protein (NMP)

The preparation of functionalized NMP is the same as in Example 8, Section IV-A. To a centrifuge tube containing 4 ml of thiolated NMP protein (9μ moles SH by Ellman assay) was added 25 mg of *E. coli* Kl-$BuA_2$-BrAc (120 nanomoles bromoacetyl/mg). The tube was sealed with a serum cap, degassed, nitrogenated and aged for 18.5 hours. It was then diluted with 6 ml of pH8 buffer and centrifuged for 2 hours as 43,000 rpm, at 4° C. in a Ti 75 rotor. The supernatant was removed and the pellet resuspended in 10 ml of pH8 buffer with Dounce homogenizer and then recentrifuged as above. The pellet from this second centrifugation was suspended in 10 ml of $H_2O$ centrifuged as above for a third time. The pellet was then resuspended in 20 ml $H_2O$.

The analysis of the conjugate was:

| Polysaccharide Concentration | Protein Concentration | Ps/Protein Ratio |
|---|---|---|
| 336 μg/ml | 1000 μg/ml | 0.34 |

SCMHC/lysine was 0.015

What is claimed is:

1. Stable, covalently-coupled polysaccharide-protein conjugates comprising polyanionic bacterial polysaccharides having acid groups and immunogenic proteins coupled through bigeneric spacers, containing thioether bonds, which may be represented by the formula A-E-S-B, wherein E is or $-\overset{O}{\overset{\|}{C}}\overset{R}{\overset{|}{C}}H-$, where R is H or $CH_3$; A is $$-\overset{W}{\overset{\|}{C}}\overset{H}{\overset{|}{N}}(CH_2)_mY(CH_2)_nNH-;$$

where m is 0 to 4, n is 0 to 3, W is O or NH, and Y is $CH_2$, O, S, NR', or $CHCO_2H$, where R' is H or $C_1$- or $C_2$-alkyl, such that when Y is $CH_2$, then both m and n are not equal to zero, and when Y is O or S, then m is 2, 3 or 4 and n is 2 or 3 and B is $$-(CH_2)_p\overset{Z}{\overset{|}{C}}H(CH_2)_qD-,$$

where p is 1 to 3, q is 0 to 2, Z is $NH_2$, $$NH\underset{\underset{O}{\|}}{C}R',$$

$CO_2H$ or H, and D is

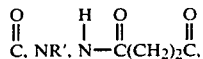

where R' is as defined above.

2. Stable, covalently-coupled polysaccharide-protein conjugates according to claim 1, wherein the bigeneric spacers may be represented by the formula,

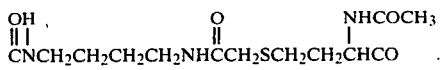

3. Polysaccharide-protein conjugates according to claim 1, wherein the bacterial capsular polysaccharide having acid groups is selected from the group consisting of *Haemophilus influenzae* type b polysaccharide, and *Streptococcus pneumoniae* types 6B, 19F and 23F polysaccharides.

4. Polysaccharide-protein conjugates according to claim 1, wherein the immunogenic protein is a meningococcal B serotype outer membrane protein or edestin protein.

5. A stable, covalently-coupled polysaccharide-protein conjugate consisting of an *Haemophilus influenzae* type b polysaccharide coupled through a spacer of the formula:

to a meningococcal B serotype outer membrane protein.

6. Polysaccharide-protein conjugates according to claim 1, wherein the bacterial capsular polysaccharide having acid groups is pneumococcal type 6B polysaccharide, the immunogenic protein is a meningococcal B serotype outer membrane protein and the bigeneric spacer may be represented by the formula,

7. Polysaccharide-protein conjugates according to claim 1, wherein the bacterial capsular polysaccharide having acid groups is pneumococcal type 19F polysaccharide, the immunogenic protein is a meningococcal B serotype outer membrane protein and the bigeneric spacer may be represented by the formula,

8. Polysaccharide-protein conjugates according to claim 1, wherein the bacterial capsular polysaccharide having acid groups is pneumococcal type 23F polysaccharide, the immunogenic protein is a meningococcal B serotype outer membrane protein and the bigeneric spacer may be represented by the formula,

9. A composition comprising an immunologically-effective amount for either active or passive protection of mammalion species from the bacteremia caused by the cognate organism, of stable, covalently-coupled polysaccharide-protein conjugates according to claim 1, antisera derived from said conjugates, or gamma-globulin or other antibody-containing fractions of said antisera, and a pharmaceutically-acceptable carrier.

10. A composition according to claim 9, further comprising an adjuvant.

11. A composition according to claim 9 or claim 10, wherein the polysaccharide-protein conjugates comprise one or more members of the group consisting of an *Haemophilus influenzae* type b polysaccharide coupled through a bigeneric spacer of the formula,

to a meningococcal B serotype outer membrane protein; a pneumococcal type 6B polysaccharide coupled through a bigeneric spacer, of the formula,

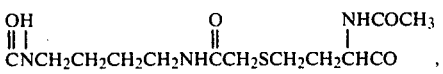

to a meningococcal B serotype outer membrane protein; a pneumococcal type 19F polysaccharide coupled through a bigeneric spacer of the formula,

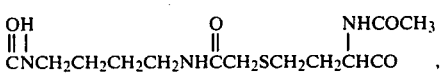

to a meningococcal B serotype outer membrane protein; and a pneumococcal type 23F polysaccharide coupled through a bigeneric spacer of the formula,

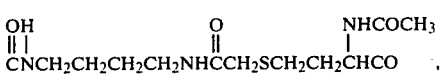

to a meningococcal B serotype outer membrane protein.

12. A composition according to claim 11, wherein an immunologically-effective amount is an amount of each of the conjugates in the composition such that each conjugate contains from 2–50 μg of the polysaccharide in the conjugate form.

13. A composition according to claim 11, wherein the mammalian species is humans.

14. A composition according to claim 12, wherein an immunologically-effective amount is an amount of each of the conjugates in the composition such that each conjugate contains 25 μg of the polysaccharide in the conjugate form for conjugates of pneumococcal polysaccharides and 10 μg of the polysaccharide in the conjugate form for conjugates of *Haemophilus influenzae* type b polysaccharide.

15. A method of treating mammalian species against the bacteremia of the cognate organisms, which comprises administering to said species an immunologically-effective amount of a composition comprising one or more types of polysaccharide-protein conjugates comprising bacterial capsular polysaccharides having acid groups coupled through bigeneric spacers, containing thioether bonds, to immunogenic proteins, and a member of the group consisting of a pharmaceutically-acceptable carrier, an adjuvant, and a pharmaceutically-acceptable carrier and adjuvant.

16. A method of treating mammalian species according to claim 15, wherein said polysaccharide-protein conjugates comprise one or more members of the group consisting of an *Haemophilus influenzae* type b polysaccharide coupled through a bigeneric spacer of the formula,

to a meningococcal B serotype outer membrane protein; a pneumococcal type 6B polysaccharide coupled through a bigeneric spacer of the formula,

to a meningococcal B serotype outer membrane protein, a pneumococcal type 19F polysaccharide coupled through a bigeneric spacer of the formula,

to a meningococcal B serotype outer membrane protein; and a pneumococcal type 23F polysaccharide coupled through a bigeneric spacer of the formula,

to a meningococcal B serotype outer membrane protein.

17. A method of treating mammalian species according to claim 15, wherein the species to be treated is human infants and children, and the effective amount of the composition in a single dose is an amount corresponding to 25 µg of the polysaccharide in the conjugate form for conjugates of pneumococcal polysaccharides and 10 µg of the polysaccharide in the conjugate form for conjugates of the *Haemophilus influenzae* type b polysaccharide-protein conjugates being administered.

18. A method of treating mammalian species according to claim 17, wherein one or two additional booster compositions of an amount of a polysaccharide-protein conjugate comprising an *Haemophilus influenzae* type b polysaccharide coupled through a bigeneric spacer of the formula,

to a meningococcal B serotype outer membrane protein corresponding to 10 µg of polysaccharide in the conjugate form may be administered to human infants and children.

19. Polysaccharide-protein conjugates according to claim 1, wherein the bacterial capsular polysaccharide having acid groups is a Group B Streptococcus type Ia, Ib, II or III polysaccharide, the immunogenic protein is a meningococcal B serotype outer membrane protein and the bigeneric spacer may be represented by the formula,

20. Polysaccharide-protein conjugates according to claim 1, wherein the bacterial capsular polysaccharide having acid groups is an *Escherichia coli* K1 polysaccharide, the immunogenic protein is a meningococcal B serotype outer membrane protein and the bigeneric spacer may be represented by the

* * * * *